United States Patent
Takada

(10) Patent No.: US 10,205,102 B2
(45) Date of Patent: *Feb. 12, 2019

(54) MATERIAL FOR ORGANIC ELECTROLUMINESCENT DEVICE AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventor: Ichinori Takada, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 59 days.

This patent is subject to a terminal disclaimer.

(21) Appl. No.: 15/076,581

(22) Filed: Mar. 21, 2016

(65) Prior Publication Data

US 2016/0372665 A1    Dec. 22, 2016

(30) Foreign Application Priority Data

Jun. 17, 2015  (JP) .................. 2015-121597

(51) Int. Cl.
  *C09K 11/06* (2006.01)
  *H01L 51/00* (2006.01)
  (Continued)

(52) U.S. Cl.
  CPC .......... *H01L 51/006* (2013.01); *C07D 307/91* (2013.01); *C09K 11/06* (2013.01);
  (Continued)

(58) Field of Classification Search
  CPC ............ C09K 11/06; C09K 2211/1011; C07D 209/86; C07D 307/91; C07D 405/12;
  (Continued)

(56) References Cited

U.S. PATENT DOCUMENTS 5,645,948 A   7/1997  Shi et al.
5,935,721 A   8/1999  Shi et al.
(Continued)

FOREIGN PATENT DOCUMENTS

EP   2 364 980 A1   9/2011
EP   2 502 908 A1   9/2012
(Continued)

OTHER PUBLICATIONS

Ji et al., Derwent 2015-003897, KR 2014145964, Dec. 24, 2014.*
(Continued)

*Primary Examiner* — Shane Fang
(74) *Attorney, Agent, or Firm* — Lewis Roca Rothgerber Christie LLP

(57) ABSTRACT

A material for an organic electroluminescent device including a monoamine derivative represented by Formula 1:

[Formula 1]

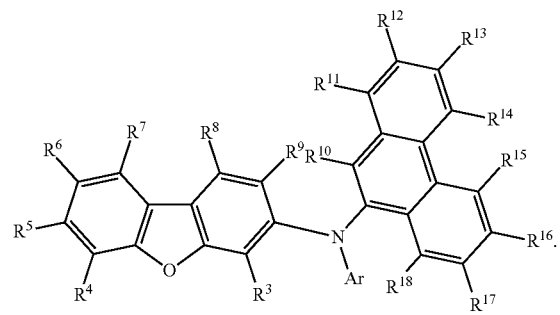

In Formula 1, Ar may be a substituted or unsubstituted aryl group having 6 to 30 carbon atoms for forming a ring, other
(Continued)

than a substituted or unsubstituted phenanthryl group, and $R^1$ to $R^{18}$ may each independently be selected from hydrogen, deuterium, a cyano group, a fluorine group (e.g., fluorine), a substituted or unsubstituted alkyl group having 1 to 10 carbon atoms, and a substituted or unsubstituted aryl group having 6 to 30 carbon atoms for forming a ring.

13 Claims, 1 Drawing Sheet

(51) Int. Cl.
  *H01L 51/50* (2006.01)
  *C07D 307/91* (2006.01)
  *B32B 9/00* (2006.01)
(52) U.S. Cl.
  CPC ...... *H01L 51/0055* (2013.01); *H01L 51/0061* (2013.01); *C09K 2211/1022* (2013.01); *C09K 2211/1088* (2013.01); *H01L 51/0052* (2013.01); *H01L 51/0058* (2013.01); *H01L 51/0073* (2013.01); *H01L 51/5012* (2013.01); *H01L 51/5056* (2013.01)
(58) Field of Classification Search
  CPC ... H01L 51/06; H01L 51/006; H01L 51/0061; H01L 51/0072; H01L 51/5012; H01L 51/5056; H01L 51/5088; H05B 33/14
  See application file for complete search history.

(56) References Cited

U.S. PATENT DOCUMENTS

| | | | |
|---|---|---|---|
| 6,465,115 | B2 | 10/2002 | Shi et al. |
| 6,596,415 | B2 | 7/2003 | Shi et al. |
| 9,181,474 | B2 | 11/2015 | Kim et al. |
| 2003/0165715 | A1 | 9/2003 | Yoon et al. |
| 2004/0265630 | A1 | 12/2004 | Suh et al. |
| 2007/0205412 | A1 | 9/2007 | Bae et al. |
| 2010/0044681 | A1 | 2/2010 | Kim et al. |
| 2010/0164371 | A1 | 7/2010 | Jeong et al. |
| 2011/0114930 | A1 | 5/2011 | Kim et al. |
| 2011/0114934 | A1 | 5/2011 | Kim et al. |
| 2012/0074395 | A1 | 3/2012 | Yabunouchi et al. |
| 2012/0175600 | A1 | 7/2012 | Yabunouchi et al. |
| 2012/0248426 | A1 | 10/2012 | Kato |
| 2012/0319091 | A1* | 12/2012 | Kato ............... C07D 307/91 257/40 |
| 2013/0200338 | A1 | 8/2013 | Kim et al. |
| 2016/0372665 | A1 | 12/2016 | Takada |
| 2017/0317289 | A1 | 11/2017 | Lee et al. |

FOREIGN PATENT DOCUMENTS

| | | |
|---|---|---|
| JP | 10-17860 | 1/1998 |
| JP | 11-87067 | 3/1999 |
| KR | 10-0691543 | 3/2007 |
| KR | 10-2007-0104086 | 10/2007 |
| KR | 10-2010-0006979 | 1/2010 |
| KR | 10-2010-0007143 | 1/2010 |
| KR | 10-2010-0071726 | 6/2010 |
| KR | 10-2011-0018195 | 2/2011 |
| KR | 10-2012-0022859 A | 3/2012 |
| KR | 10-2012-0052993 A | 5/2012 |
| KR | 10-1516062 B1 | 4/2015 |
| WO | WO 2010/061824 A1 | 6/2010 |
| WO | WO 2010/114017 A1 | 10/2010 |
| WO | WO 2011/021520 A1 | 2/2011 |
| WO | WO 2011/059099 A1 | 5/2011 |
| WO | WO 2011/133007 A2 | 10/2011 |
| WO | WO 2012/091471 A2 | 7/2012 |
| WO | WO 2013/039184 A1 | 3/2013 |
| WO | WO 2014/088047 A1 | 6/2014 |
| WO | WO 2015/041492 A1 | 3/2015 |

OTHER PUBLICATIONS

Machine Translation of WO 2013/039184 A1.
Machine Translation of WO 2014/088047 A1.
U.S. Office Action dated Aug. 15, 2018, issued in U.S. Appl. No. 15/166,151, 28 pages.
U.S. Office Action dated Feb. 20, 2015, issued in U.S. Appl. No. 13/598,489 (11 pages).

* cited by examiner

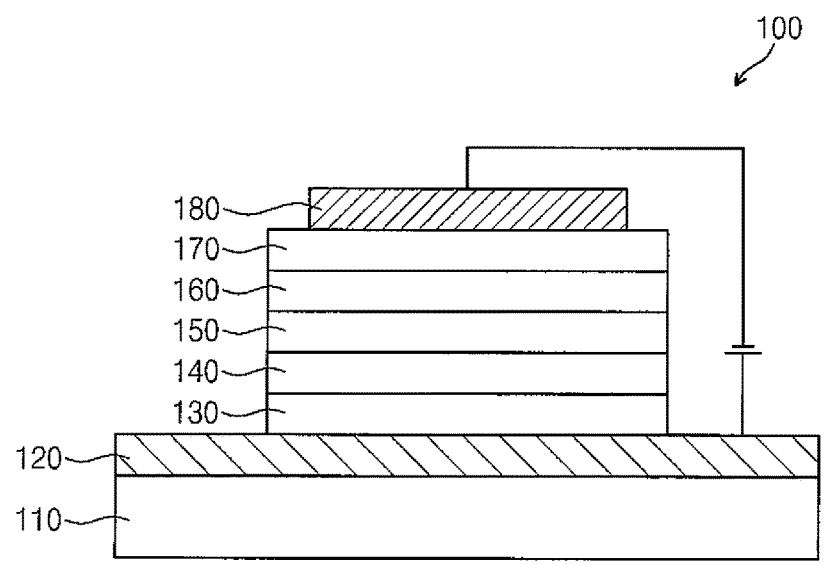

MATERIAL FOR ORGANIC ELECTROLUMINESCENT DEVICE AND ORGANIC ELECTROLUMINESCENT DEVICE INCLUDING THE SAME

CROSS-REFERENCE TO RELATED APPLICATIONS

This patent application claims priority to and the benefit of Japanese Patent Application No. 2015-121597, filed on Jun. 17, 2015 in the Japan Patent Office, the entire content of which is incorporated herein by reference.

BACKGROUND

One or more aspects of embodiments of the present disclosure are related to a material for an organic electroluminescent device and an organic electroluminescent device including the same.

Organic electroluminescent displays have been a recent focus of development. Organic electroluminescent devices, which are self-luminescent devices used in organic electroluminescent displays, have also been a focus of development.

An example structure of an organic electroluminescent device may be obtained by sequentially laminating (or stacking) an anode, a hole injection layer, a hole transport layer, an emission layer, an electron transport layer, an electron injection layer, and a cathode. In such an organic electroluminescent device, holes and electrons injected from the anode and the cathode, respectively, may recombine in the emission layer to generate excitons and thereby emit light via the transition (e.g., radiative decay) of the generated excitons to a ground state.

In order to improve the emission lifetime of an organic electroluminescent device, various compounds have been examined for use in each layer. For example, an amine compound has been used as a hole transport material of an organic electroluminescent device in the related art.

SUMMARY

An organic electroluminescent device using an amine compound in the related art as a hole transport material has insufficient emission lifetime. Accordingly, a material capable of improving the emission lifetime of an organic electroluminescent device is desired.

One or more aspects of embodiments of the present disclosure are directed toward a novel and improved material for an organic electroluminescent device that is capable of increasing the emission lifetime of an organic electroluminescent device, and an organic electroluminescent device including the same.

One or more aspects of embodiments of the present disclosure provide a material for an organic electroluminescent device, including a monoamine derivative represented by Formula 1:

[Formula 1]

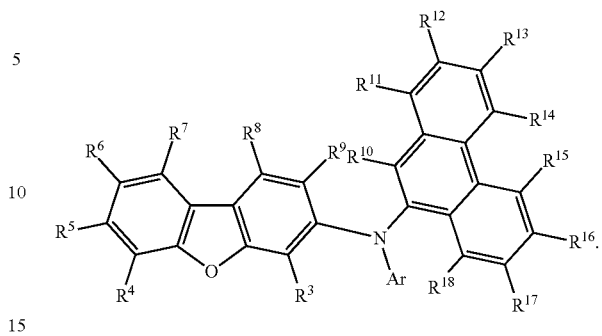

In Formula 1, Ar may be a substituted or unsubstituted aryl group having 6 to 30 carbon atoms for forming a ring, other than a substituted or unsubstituted phenanthryl group, and $R^1$ to $R^{18}$ may each independently be selected from hydrogen, deuterium, a cyano group, a fluorine group (e.g., fluorine), a substituted or unsubstituted alkyl group having 1 to 10 carbon atoms, and a substituted or unsubstituted aryl group having 6 to 30 carbon atoms for forming a ring.

According to an aspect of the present disclosure, the emission lifetime of an organic electroluminescent device may be increased.

In one embodiment, Ar may be an aryl group other than an aryl-substituted phenyl group.

According to an aspect of the present disclosure, the emission lifetime of an organic electroluminescent device may be increased.

In one embodiment, Ar may be a substituted or unsubstituted phenyl group, biphenyl group, terphenyl group, or quaterphenyl group.

According to an aspect of the present disclosure, the emission lifetime of an organic electroluminescent device may be increased.

In one embodiment, Ar may be a substituted or unsubstituted naphthyl group, naphthyl phenyl group, ternaphthyl group, binaphthyl group, or naphthyl biphenyl group.

According to an aspect of the present disclosure, the emission lifetime of an organic electroluminescent device may be increased.

One or more embodiments of the present disclosure provide an organic electroluminescent device including the material for an organic electroluminescent device in at least one layer.

In one embodiment of the present disclosure, an organic electroluminescent device includes a first electrode, a second electrode on the first electrode, and one or more organic layers between the first electrode and the second electrode, in which at least one layer selected from the one or more organic layers includes the material for an organic electroluminescent device.

According to an aspect of the present disclosure, the emission lifetime of an organic electroluminescent device may be increased.

One or more embodiments of the present disclosure provide an organic electroluminescent device including the material for an organic electroluminescent device in at least one layer between an anode and an emission layer.

In one embodiment, an emission layer may be between the first electrode and the second electrode, and the material for an organic electroluminescent device may be included in at least one layer between the first electrode and the emission layer.

In one embodiment, the emission layer may include a blue light emitting material.

According to an aspect of the present disclosure, the emission lifetime of an organic electroluminescent device may be increased.

In one embodiment, the organic layer including the material for an organic electroluminescent device may be included in at least one selected from a hole injection layer and a hole transport layer.

According to an aspect of the present disclosure, the emission lifetime of an organic electroluminescent device may be increased.

BRIEF DESCRIPTION OF THE DRAWING

The accompanying drawing is included to enable further understanding of the present disclosure, and is incorporated in and constitutes a part of this specification. The drawing illustrates example embodiments of the present disclosure and, together with the description, serves to explain principles of the present disclosure. In the drawing:

The drawing is a schematic diagram showing an organic electroluminescent device according an embodiment of the present disclosure.

DETAILED DESCRIPTION

Example embodiments of the present disclosure will be described below in more detail with reference to the accompanying drawing. In the specification and drawing, elements having substantially the same function will be designated by the same reference numerals, and repeated explanations thereof will not be provided.

The thicknesses of layers, films, panels, regions, etc., may be exaggerated in the drawings for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

1. Components of Material for Organic Electroluminescent Device

The emission lifetime of an organic electroluminescent device may be increased when the material for an organic electroluminescent device is used as a hole transport material. First, the components of the material for an organic electroluminescent device according to an embodiment of the present disclosure will be explained.

The material for an organic electroluminescent device according to an embodiment of the present disclosure may include a monoamine derivative represented by Formula 1:

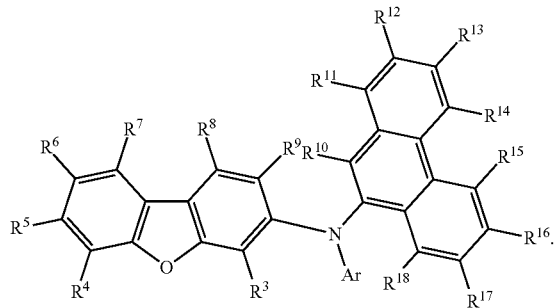

[Formula 1]

In Formula 1,

Ar may be a substituted or unsubstituted aryl group having 6 to 30 carbon atoms for forming a ring, other than a substituted or unsubstituted phenanthryl group, and $R^1$ to $R^{18}$ may each independently be selected from hydrogen, deuterium, a cyano group, a fluorine group (e.g., fluorine), a substituted or unsubstituted alkyl group having 1 to 10 carbon atoms, and a substituted or unsubstituted aryl group having 6 to 30 carbon atoms for forming a ring. As used herein, "atoms for forming a ring" may refer to "ring-forming atoms".

For example, in the monoamine derivative according to an embodiment of the present disclosure, the nitrogen atom of the monoamine derivative may be combined (e.g., coupled) with carbon at position 9 of a phenanthryl group and with carbon at position 3 of a dibenzofuranyl group.

In Formula 1, Ar may be a substituted or unsubstituted phenyl group, biphenyl group, terphenyl group, quaterphenyl group, naphthyl group, anthryl group, indenyl group, pyrenyl group, fluoranthenyl group, triphenylenyl group, perylenyl group, biphenylenyl group, naphthyl phenyl group, naphthyl biphenyl group, ternaphthyl group, binaphthyl phenyl group, or fluorenyl group.

In some embodiments, Ar may be an aryl group other than an aryl-substituted phenyl group. For example, Ar may be a substituted or unsubstituted naphthyl group, naphthyl phenyl group, ternaphthyl group, binaphthyl phenyl group, or naphthyl biphenyl group. In some embodiments, Ar may be a substituted or unsubstituted naphthyl phenyl group.

In some embodiments, Ar may be a substituted or unsubstituted phenyl group, biphenyl group, terphenyl group, or quaterphenyl group. However, embodiment of the present disclosure are not limited thereto.

Non-limiting examples of the Ar aryl group substituent may include deuterium, a halogen atom (for example, fluorine, chlorine, etc.), an alkyl group (for example, methyl, ethyl, propyl, butyl, etc.), an alkenyl group (for example, vinyl, etc.), a silyl group (for example, trimethylsilyl, etc.), a cyano group, an alkoxy group (for example, methoxy, butoxy, etc.), a nitro group, a hydroxyl group, a thiol group, and an aryl group (for example, phenyl, naphthyl, terphenyl, fluorenyl, etc.), etc. The alkyl group may be selected from a linear alkyl group (for example, methyl, ethyl, propyl, butyl, octyl, decyl, pentadecyl, etc.), and a branched alkyl group (for example, t-butyl, etc.). The substituent may be itself substituted with one or more selected from the same substituents. In some embodiments, adjacent substituents may combine (e.g., couple) with each other to form a ring.

In Formula 1, $R_1$ to $R_{18}$ may each independently be selected from hydrogen, deuterium, a cyano group, a fluorine group (e.g., fluorine), a substituted or unsubstituted alkyl group having 1 to 10 carbon atoms, and a substituted or unsubstituted aryl group having 6 to 30 carbon atoms for forming a ring. The substituted alkyl group having 1 to 10 carbon atoms may be substituted with the same substituents available for the Ar aryl group. In addition, the same substituted or unsubstituted aryl groups having 6 to 30 carbon atoms available for the Ar aryl group may also be used for $R_1$ to $R_{18}$.

The monoamine derivative represented by Formula 1 according to an embodiment of the present disclosure may improve the emission lifetime of an organic electroluminescent device when an emission layer includes a blue light emitting material.

In some embodiments, the material for an organic electroluminescent device according to an embodiment of the present disclosure may be included in one or more layers of the organic electroluminescent device. In some embodiments, the material for an organic electroluminescent device may be included in at least one layer between an emission layer and an anode of the organic electroluminescent device. For example, the material for an organic electroluminescent device may be included in one selected from the hole transport layer and the hole injection layer of the organic electroluminescent device. However, embodiments of the layer including the material for an organic electroluminescent device are not limited thereto. For example, the material for an organic electroluminescent device may be included in any organic layer between the anode and the cathode of an organic electroluminescent device.

An organic electroluminescent device using the material for an organic electroluminescent device having the above-described components may have an improved emission lifetime, as described in the following embodiments. The monoamine derivative represented by Formula 1 may be at least one selected from Compounds 1 to 35. However, embodiments of the monoamine derivative are not limited thereto.

1

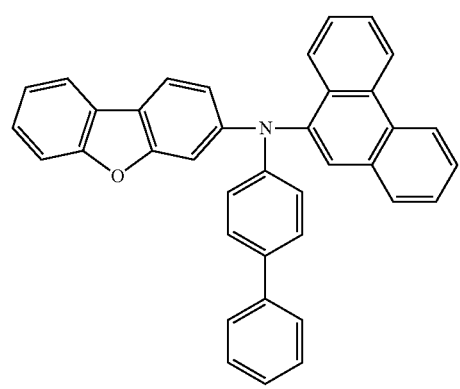

-continued

2

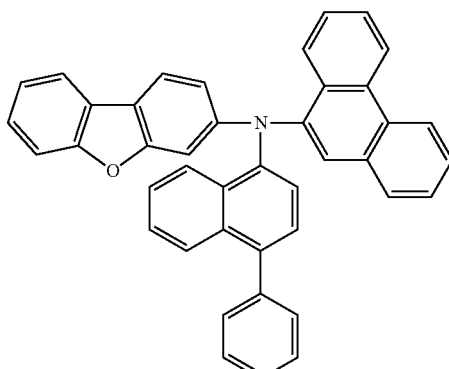

3

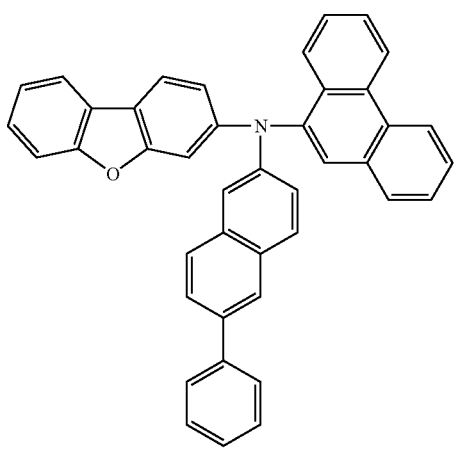

4

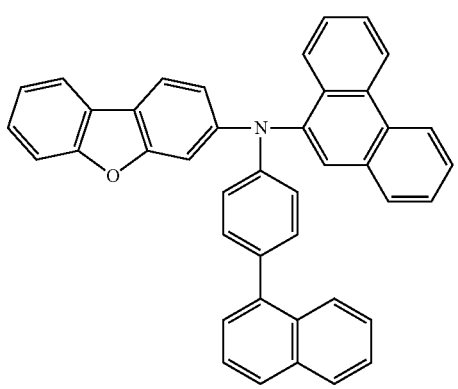

5

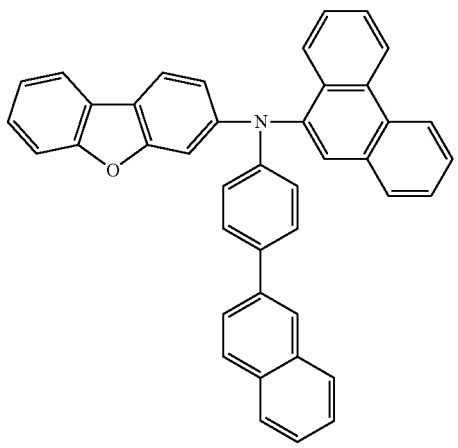

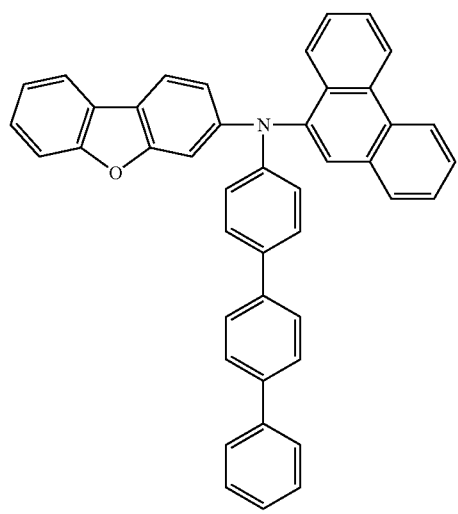
6
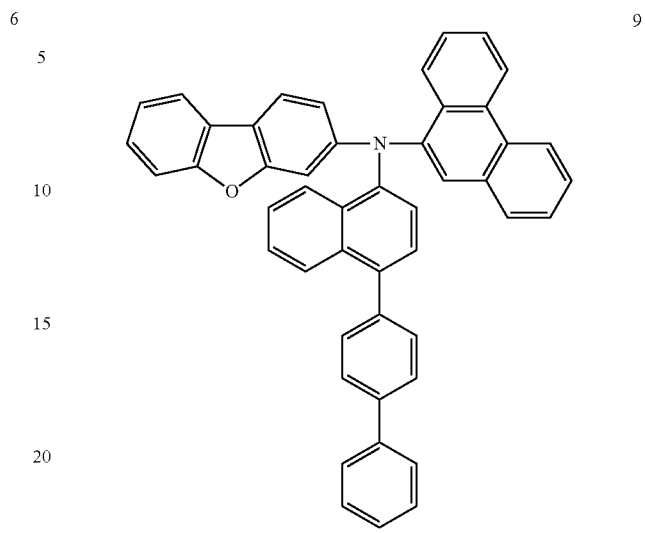
9
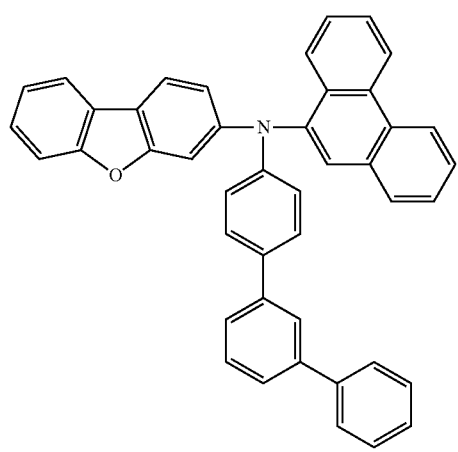
7
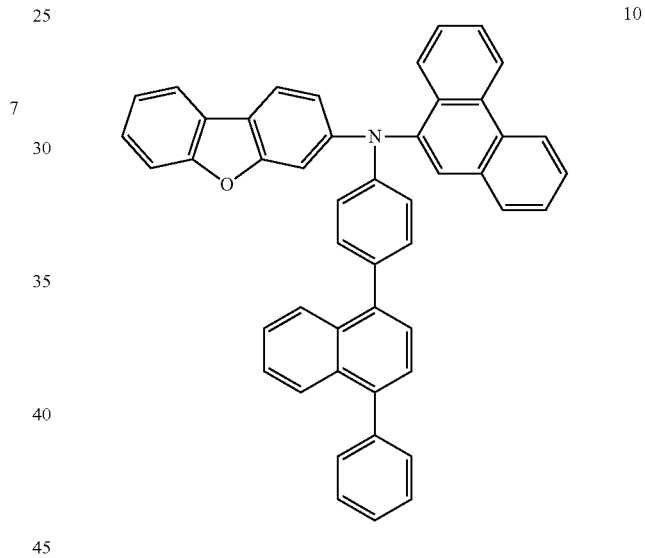
10
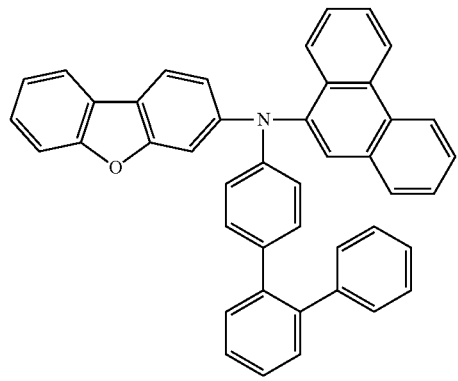
8
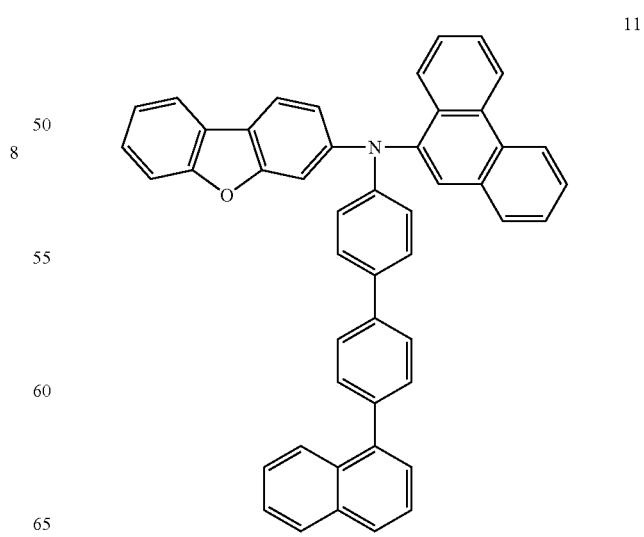
11

12
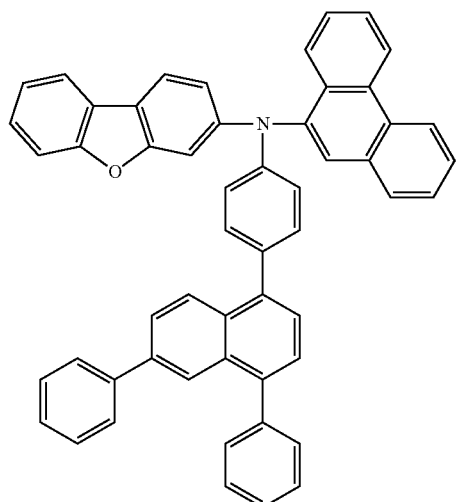
13
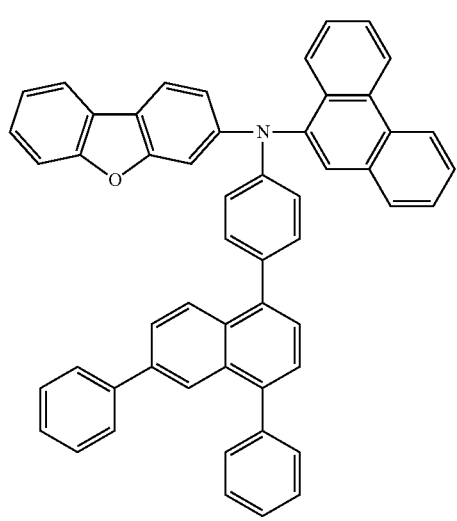
14
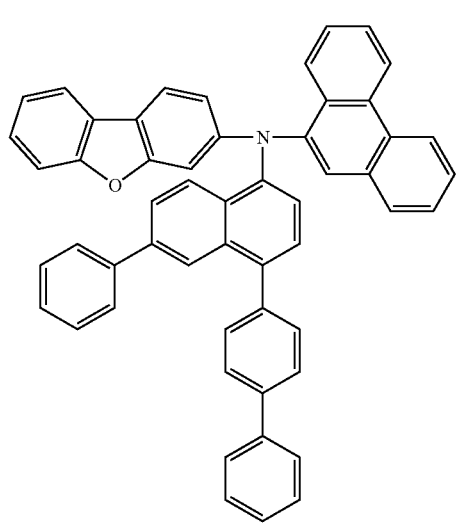
15
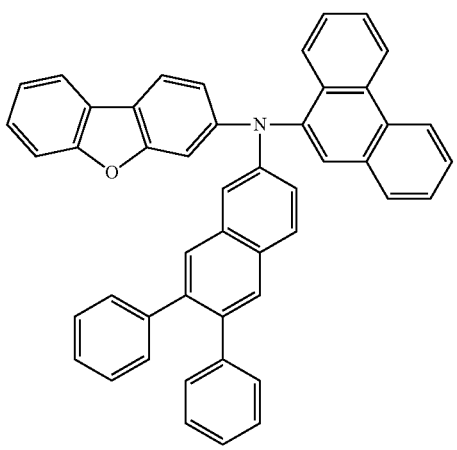
16
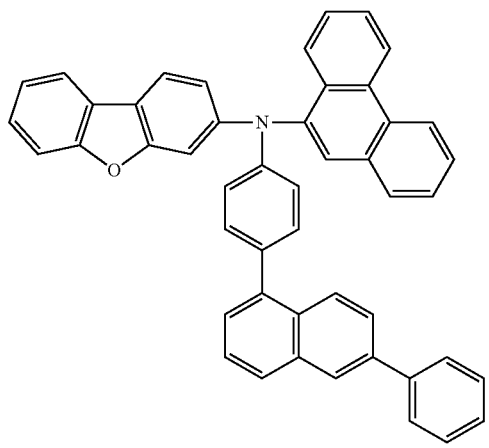
17
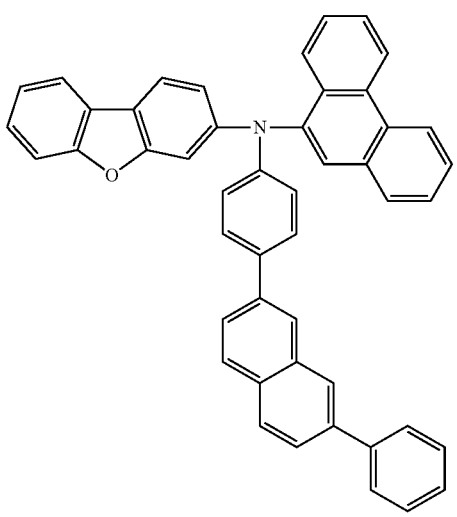

18
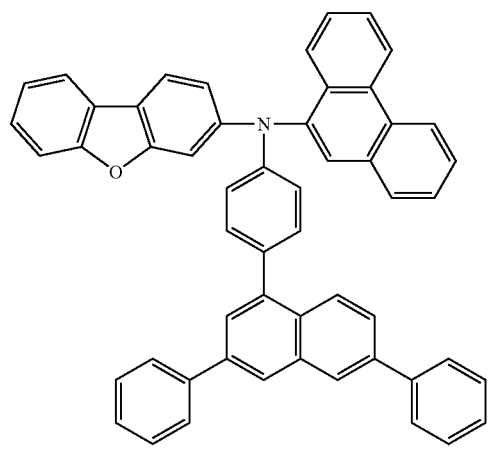
19
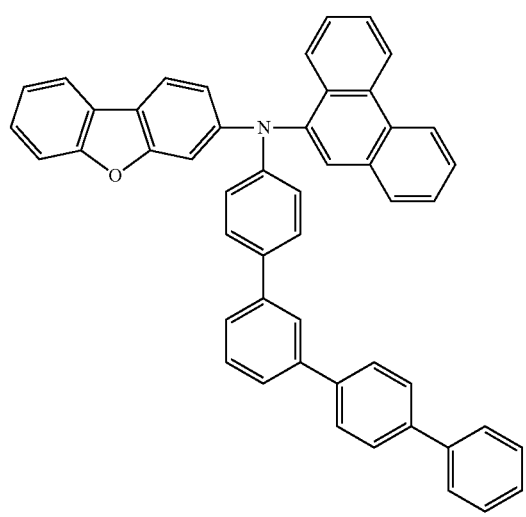
20
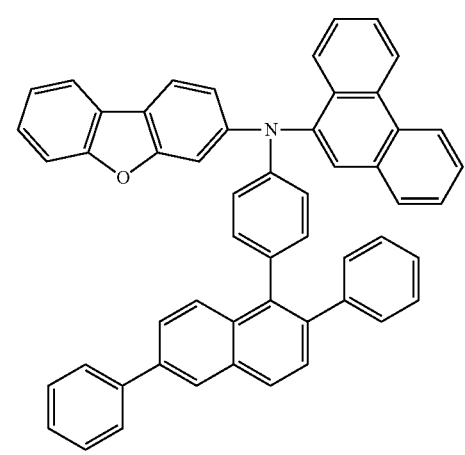
21
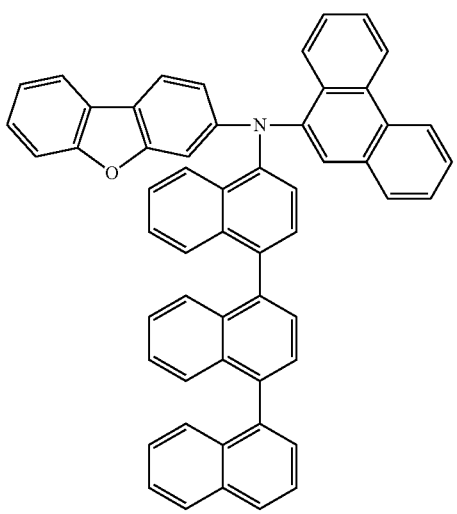
22
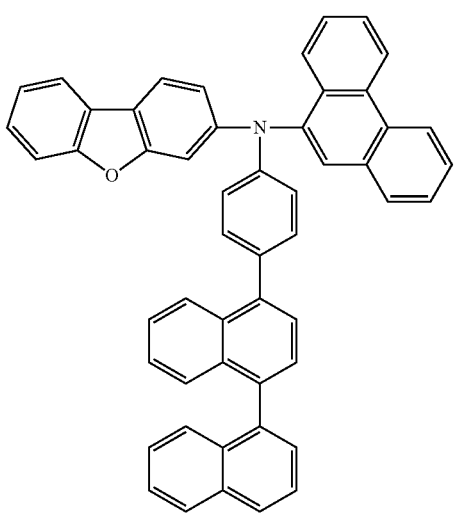
23
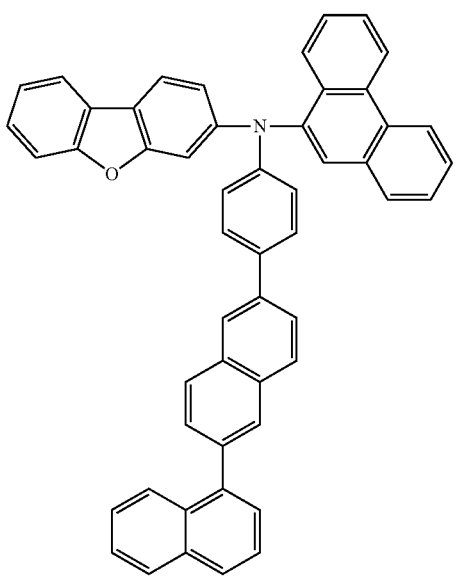

24
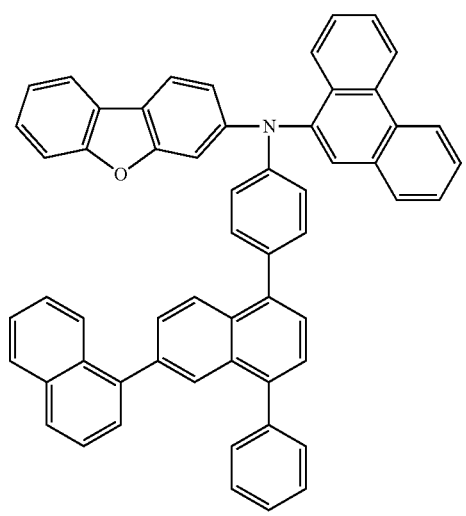
25
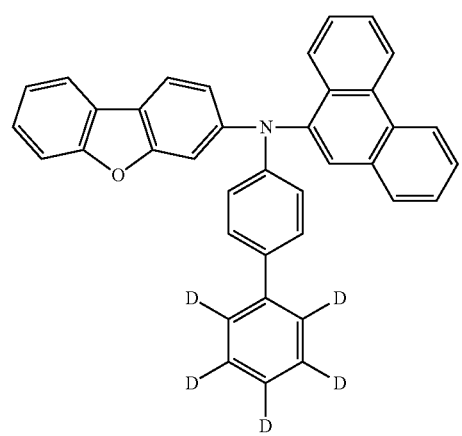
26
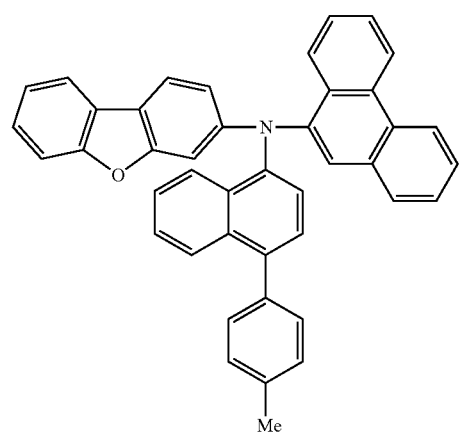
27
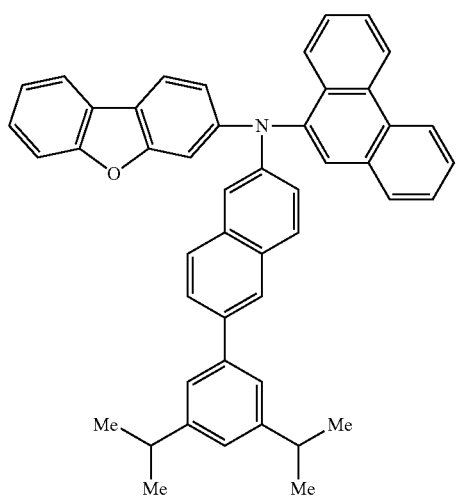
28
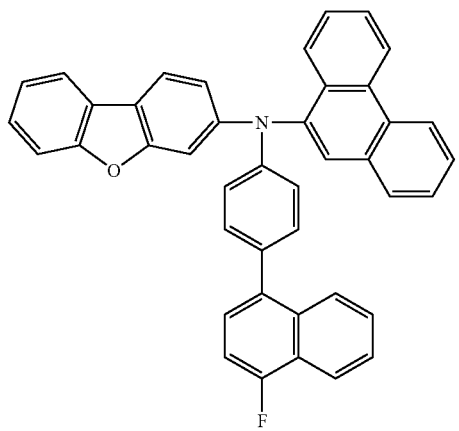
29
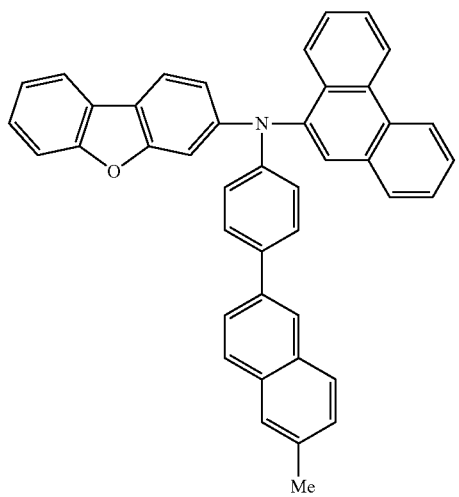

30
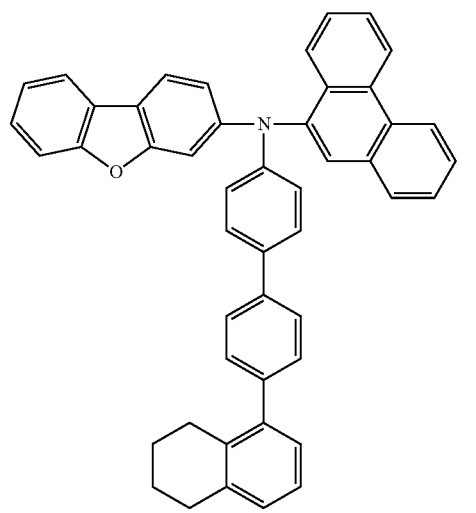
31
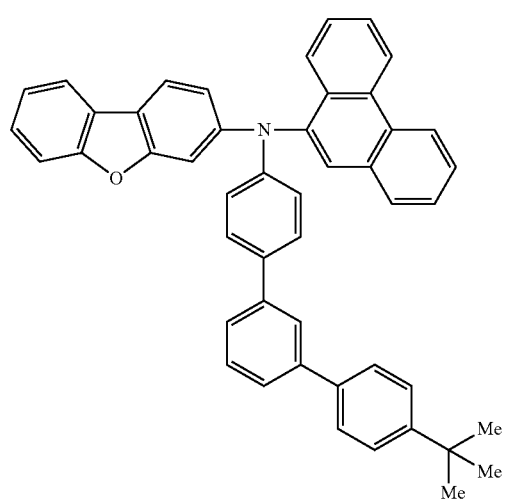
32
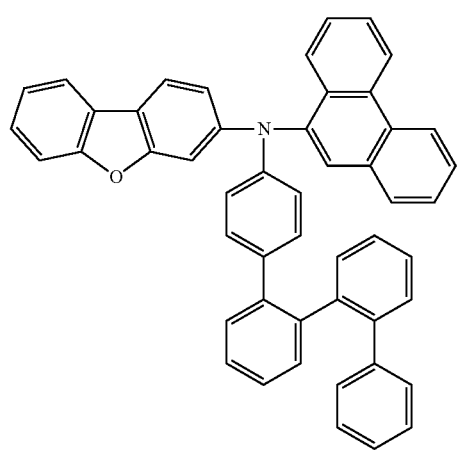
33
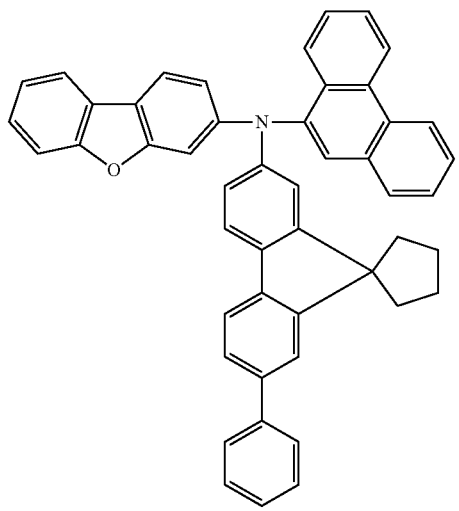
34
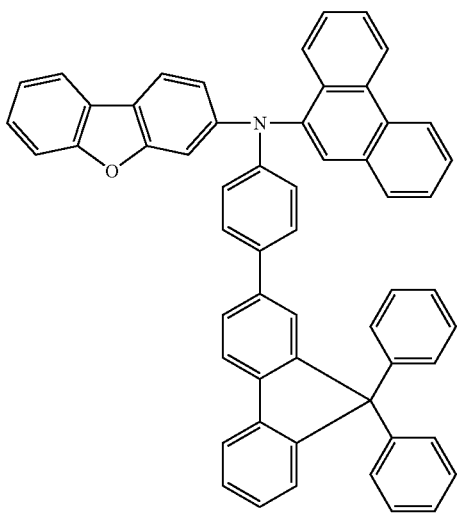
35
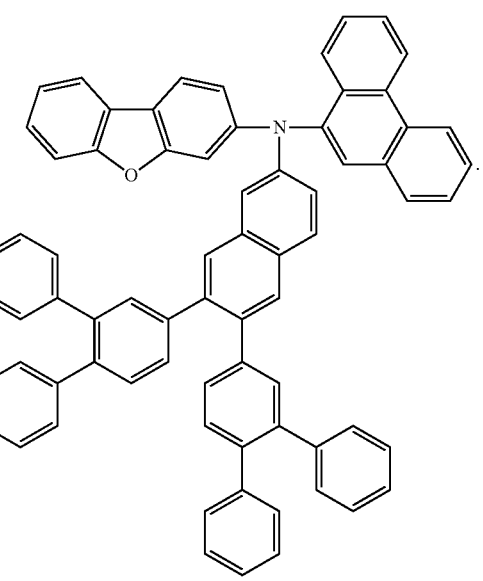
The monoamine derivative according to an embodiment of the present disclosure may be synthesized by Reactions 1 to 3. In some embodiments, the monoamine derivative according to an embodiment of the present disclosure may be synthesized by one selected from Reactions 1 to 3 depending on the supply conditions of raw materials, etc.

[Reaction 1]

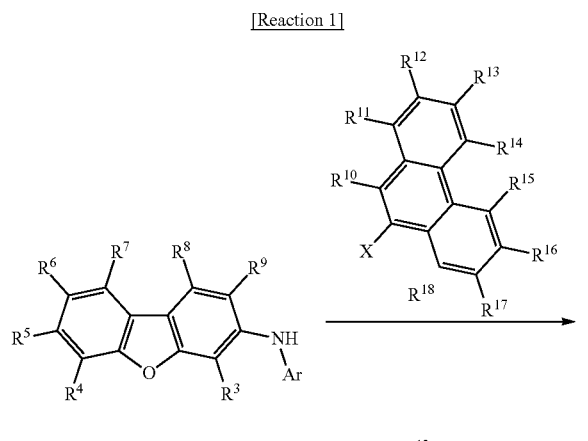

[Reaction 2]

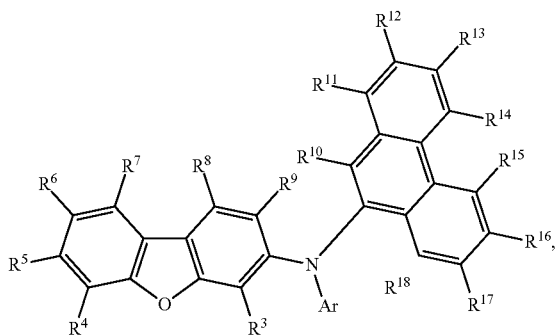

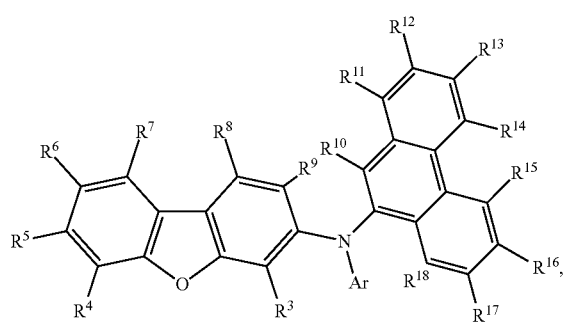

[Reaction 3]

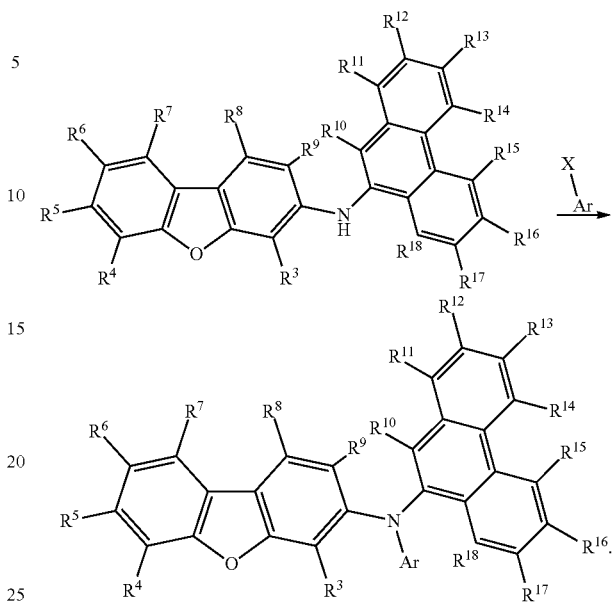

In Reactions 1 to 3, X may be a halogen atom, etc., and the monoamine derivative according to an embodiment of the present disclosure may be synthesized via the coupling reaction of two compounds.

Embodiments of the synthesis of the monoamine derivative according to an embodiment of the present disclosure are not limited to the synthetic examples of Reactions 1 to 3.

2. Organic Electroluminescent Device Using the Material for Organic Electroluminescent Device Hereinafter, an organic electroluminescent device using the material for an organic electroluminescent device according to an embodiment of the present disclosure will be described in more detail with reference to the drawing. The drawing is a schematic cross-sectional view of an organic electroluminescent device according to an embodiment of the present disclosure.

As shown in the drawing, an organic electroluminescent device 100 according to an embodiment of the present disclosure may include a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

Here, the monoamine derivative according to an embodiment of the present disclosure may be included in, for example, at least one selected from the hole injection layer 130 and the hole transport layer 140. In one embodiment, the monoamine derivative according to an embodiment of the present disclosure may be included in both layers. In one embodiment, the monoamine derivative according to an embodiment of the present disclosure may be included in the hole transport layer 140 adjacent to the emission layer 150.

Each organic thin layer between the first electrode 120 and the second electrode 180 of the organic electroluminescent device 100 may be formed by one or more suitable methods, such as an evaporation method.

The substrate 110 may be any suitable substrate available in the art for an organic electroluminescent device. For example, the substrate 110 may be selected from a glass substrate, a semiconductor substrate, and a transparent plastic substrate.

The first electrode 120 may be on the substrate 110. The first electrode 120 may be an anode and may be formed as a transmission type (e.g., transmission) electrode using a metal, an alloy, a conductive compound, etc. having a high work function. The first electrode 120 may be formed using, for example, transparent and highly conductive indium tin oxide (ITO), indium zinc oxide (IZO), tin oxide ($SnO_2$), zinc oxide (ZnO), etc. In some embodiments, the first electrode 120 may be formed as a reflective type (e.g., reflective) electrode using magnesium (Mg), aluminum (Al), etc.

The hole injection layer 130 may be on the first electrode 120. The hole injection layer 130 may facilitate easy injection of holes from the first electrode 120 and may be formed, for example, to a thickness of about 10 nm to about 150 nm.

The hole injection layer 130 may be on the first electrode 120. The hole injection layer 130 may facilitate easy injection of holes from the first electrode 120 and may be formed, for example, to a thickness of about 10 nm to about 150 nm. The hole injection layer 130 may be formed using the monoamine derivative according to an embodiment of the present disclosure or using any suitable material available in the art. Non-limiting examples of such material may include, for example, triphenylamine-containing polyether ketone (TPAPEK), 4-isopropyl-4'-methyldiphenyliodoniumtetrakis (pentaflorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound (such as copper phthalocyanine), 4,4',4"-tris(3-methylphenylamino) triphenylamine (m-MTDATA), N,N'-di(1-naphthyl)-N,N'-diphenylbenzidine (NPB), 4,4',4"-tris{N,N-diamino}triphenylamine (TDATA), 4,4',4"-tris (N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphorsulfonic acid (PANI/CSA), polyaniline/poly(4-styrenesulfonate (PANI/PSS), etc.

The hole transport layer 140 may be on the hole injection layer 130. The hole transport layer 140 may include a hole transport material having the function of transporting holes and may be formed, for example, to a thickness of about 10 nm to about 150 nm. The hole transport layer 140 may be provided as a plurality of layers.

The hole transport layer 140 may include the monoamine derivative according to an embodiment of the present disclosure. When the hole injection layer 130 includes the monoamine derivative according to an embodiment of the present disclosure, the hole transport layer 140 may include a suitable hole transport material available in the related art. Non-limiting examples of such hole transport material may include 1,1-bis[(di-4-tolylamino)phenyl]cyclohexane (TAPC), a carbazole derivative (such as N-phenyl carbazole and/or polyvinyl carbazole), N, N'-bis(3-methylphenyl)-N, N'-diphenyl-[1,1-biphenyl]-4,4'-diamine (TPD), 4,4',4"-tris (N-carbazolyl)triphenylamine (TCTA), N,N'-di(1-naphthyl)-N,N'-diphenylbenzidine (NPB), etc.

The emission layer 150 may be provided on the hole transport layer 140. The emission layer 150 may emit light via fluorescence, phosphorescence, etc. and may be formed to a thickness of about 10 nm to about 60 nm. The material of the emission layer 150 may be any suitable luminescent material available in the related art (such as a fluoranthene derivative, a styryl derivative, a pyrene derivative, an arylacetylene derivative, a fluorene derivative, a perylene derivative, and/or a chrysene derivative). In some embodiments, a styryl derivative, a pyrene derivative, a perylene derivative, and/or an anthracene derivative may be used. For example, an anthracene derivative represented by Formula 2 may be used as the material of the emission layer 150:

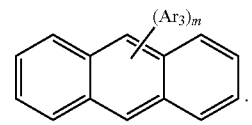

[Formula 2]

In the above Formula 2, each $Ar_3$ may be independently selected from hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 carbon atoms for forming a ring, a substituted or unsubstituted silyl group, a carboxyl group, a halogen atom, a cyano group, a nitro group, and a hydroxyl group, and m may be an integer selected from 1 to 10.

For example, each $Ar_3$ may independently be a phenyl group, a biphenyl group, a terphenyl group, a naphthyl group, a phenyl naphthyl group, a naphthyl phenyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzoimidazolyl group, a pyrazolyl group, a dibenzofuranyl group, a dibenzothienyl group, etc. In some embodiments, each $Ar_3$ may independently be a phenyl group, a biphenyl group, a terphenyl group, a fluorenyl group, a carbazolyl group, a dibenzofuranyl group, etc.

The compound represented by Formula 2 may be one selected from Compounds a-1 to a-12. However, embodiments of the compound represented by Formula 2 are not limited thereto.

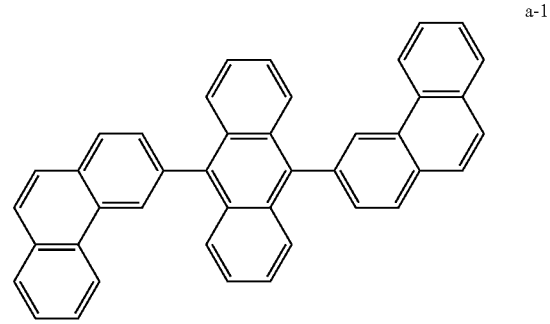

a-1

-continued
a-2
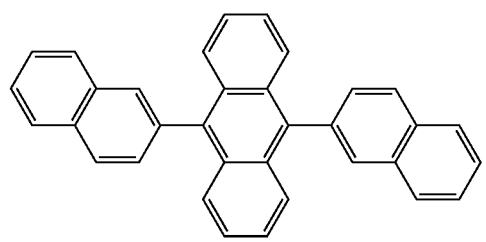
a-3
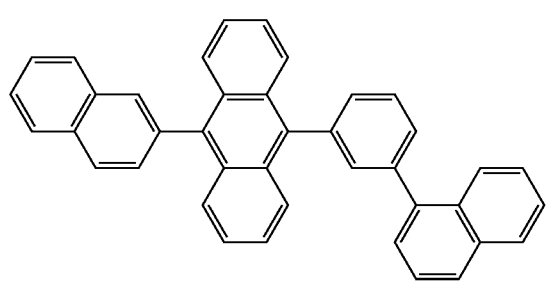
a-4
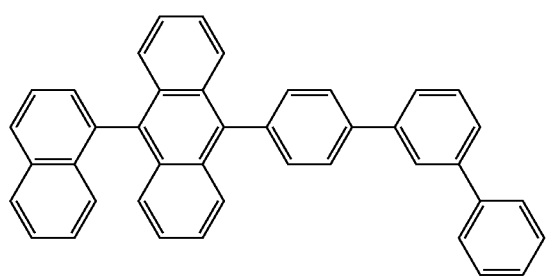
a-5
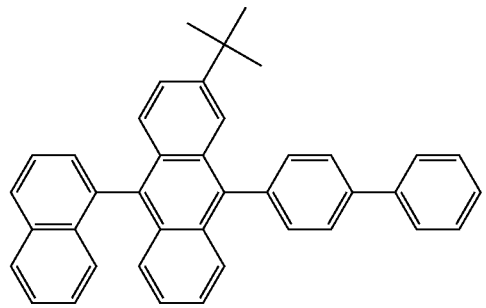
a-6
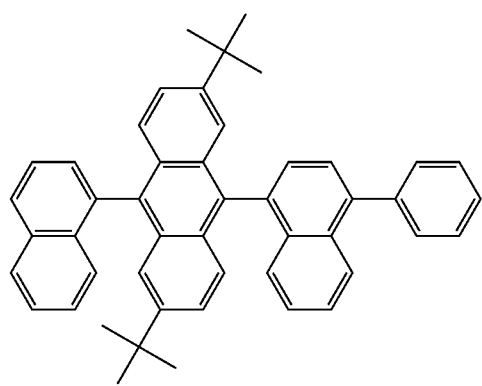
a-7
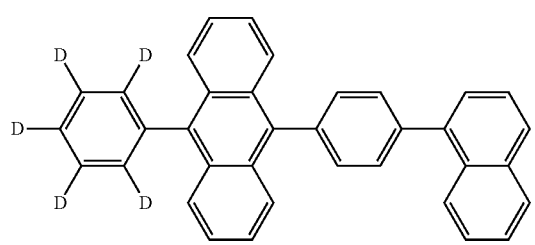
a-8
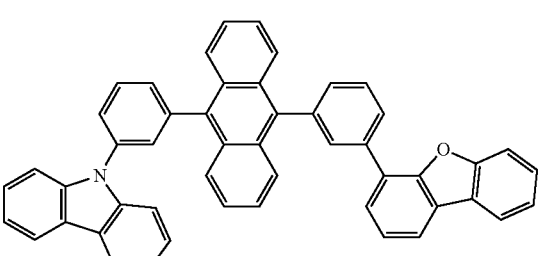
a-9
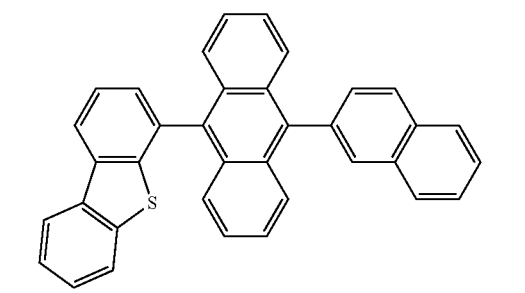
a-10
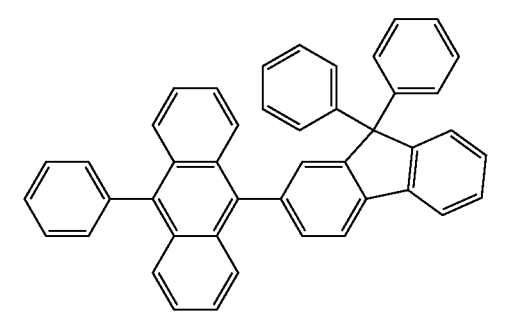
a-11
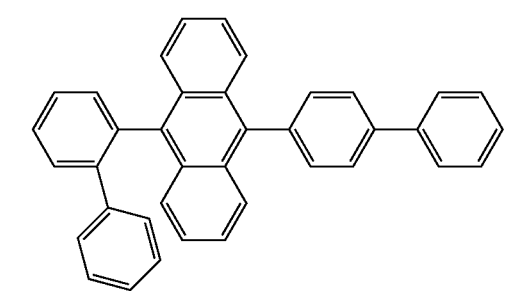

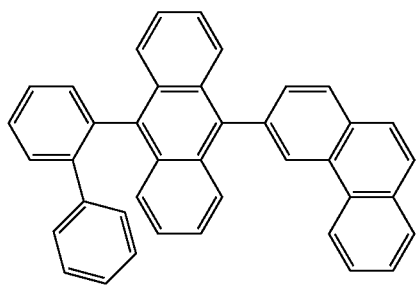

a-12

The emission layer 150 may include a styryl derivative (such as 1,4-bis[2-(3-N-ethylcarbazolyl)vinyl]benzene (BC-zVB), 4'-(di-p-tolylamino)-4-[(di-p-tolylamino)styryl]stilbene (DPAVB), and/or N-(4-((E)-2-(6-((E)-4-(diphenylamino)styryl) naphthalene-2-yl)vinyl)phenyl)-N-phenylbenzeneamine (N-BDAVD)), a perylene derivative (such as 2,5,8,11-tetra-t-butylperylene (TBPe)), and a pyrene derivative (such as 1,1'-dipyrene, 1,4-dipyrenylbenzene and/or 1,4-bis(N,N-diphenylamino)pyrene), but embodiments of the present disclosure are not limited thereto.

An electron transport layer 160 may be on the emission layer 150. The electron transport layer 160 may include an electron transport material having the function of transporting electrons, and may have a thickness of about 15 nm to about 50 nm.

The electron transport layer 160 may include an electron transport material. Non-limiting examples of suitable electron transport materials may include tris(8-hydroxyquinolinato) aluminum (Alq3), a material having a nitrogen-containing aromatic ring, etc. Non-limiting examples of the material having a nitrogen-containing aromatic ring may include a material including a pyridine ring (such as 1,3,5-tri[(3-pyridyl)-phen-3-yl]benzene), a material including a triazine ring (such as 2,4,6-tris(3'-(pyridin-3-yl)biphenyl-3-yl)-1,3,5-triazine), and a material including an imidazole derivative (such as 2-(4-(N-phenylbenzoimidazolyl-1-yl-phenyl)-9,10-dinaphthylanthracene)).

The electron injection layer 170 may be provided on the electron transport layer 160. The electron injection layer 170 may facilitate easy injection of electrons from the second electrode 180 and may have a thickness of about 0.3 nm to about 9 nm. The electron injection layer 170 may include any suitable material available in the art. For example, the electron injection layer 170 may include a Li complex (such as lithium-8-quinolinato (Liq) and/or lithium fluoride (LiF)), sodium chloride (NaCl), cesium fluoride (CsF), lithium oxide ($Li_2O$), and/or barium oxide (BaO).

In some embodiments, the second electrode 180 may be on the electron injection layer 170. The second electrode 180 may be, for example, a cathode, and may be formed as a reflective type (e.g., reflective) electrode using a metal, an alloy, a conductive compound, etc. having a low work function. The second electrode 180 may be formed using a metal (such as lithium (Li), magnesium (Mg), aluminum (Al), and/or calcium (Ca)), and/or a mixture of metals (such as aluminum-lithium (Al—Li), magnesium-indium (Mg—In), and/or magnesium-silver (Mg—Ag)). In some embodiments, the second electrode 180 may be formed as a transmission type electrode using ITO, IZO, etc.

Each of the above-mentioned layers may be formed by selecting an appropriate or suitable layer forming method (such as a vacuum evaporation method, a sputtering method, and/or various other coating methods) depending on the materials to be used.

The structure of the organic electroluminescent device 100 according to an embodiment of the present disclosure was explained as described above. The organic electroluminescent device 100 including the monoamine derivative according to an embodiment of the present disclosure may have an increased emission lifetime.

The structure of the organic electroluminescent device 100 according to an embodiment of the present disclosure is not limited to the above-described embodiments. The organic electroluminescent device 100 according to another embodiment of the present disclosure may be formed using the structures of other organic electroluminescent devices in the related art. For example, the organic electroluminescent device 100 may omit one or more layers selected from the hole injection layer 130, the electron transport layer 160, and the electron injection layer 170, and/or may include additional layers. In some embodiments, each layer of the organic electroluminescent device 100 may be formed as a single layer or as a plurality of layers.

In some embodiments, the organic electroluminescent device 100 may include a hole blocking layer between the electron transport layer 160 and the emission layer 150 to prevent or reduce diffusion of triplet excitons and/or holes into the electron transport layer 160. In some embodiments, the hole blocking layer may be formed using, for example, an oxadiazole derivative, a triazole derivative, or a phenanthroline derivative.

EXAMPLES

Hereinafter, the organic electroluminescent device according to an embodiment of the present disclosure will be explained in more detail by referring to examples and comparative examples. However, the following examples are provided only for illustration of the organic electroluminescent device according to embodiments of the present disclosure, and embodiments of the organic electroluminescent device are not limited thereto.

[Synthesis of Monoamine Derivatives]

First, the synthetic method of the monoamine derivative according to an embodiment of the present disclosure will be described in more detail by referring to Compounds 1, 4, 6, 7, and 34. The following synthetic methods are only for illustration, and embodiments of the synthetic method of the monoamine derivative according to an embodiment of the present disclosure are not limited thereto.

(Synthesis of Compound 1)

Compound 1, a monoamine derivative according to an embodiment of the present disclosure, was synthesized according to Reaction 4:

[Reaction 4]

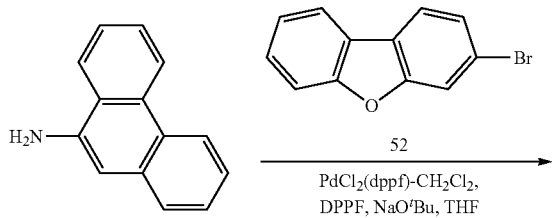

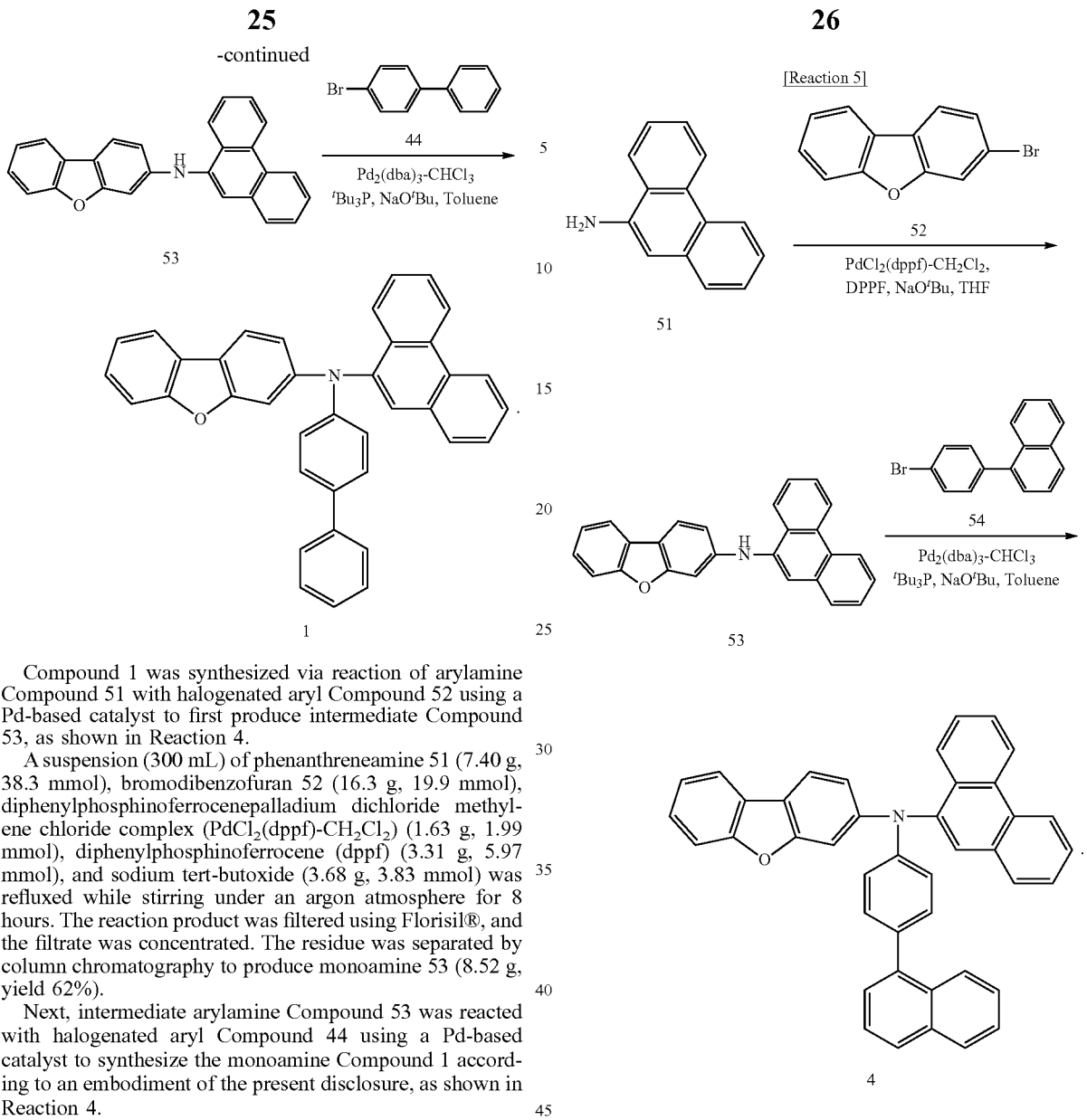

Compound 1 was synthesized via reaction of arylamine Compound 51 with halogenated aryl Compound 52 using a Pd-based catalyst to first produce intermediate Compound 53, as shown in Reaction 4.

A suspension (300 mL) of phenanthreneamine 51 (7.40 g, 38.3 mmol), bromodibenzofuran 52 (16.3 g, 19.9 mmol), diphenylphosphinoferrocenepalladium dichloride methylene chloride complex (PdCl$_2$(dppf)-CH$_2$Cl$_2$) (1.63 g, 1.99 mmol), diphenylphosphinoferrocene (dppf) (3.31 g, 5.97 mmol), and sodium tert-butoxide (3.68 g, 3.83 mmol) was refluxed while stirring under an argon atmosphere for 8 hours. The reaction product was filtered using Florisil®, and the filtrate was concentrated. The residue was separated by column chromatography to produce monoamine 53 (8.52 g, yield 62%).

Next, intermediate arylamine Compound 53 was reacted with halogenated aryl Compound 44 using a Pd-based catalyst to synthesize the monoamine Compound 1 according to an embodiment of the present disclosure, as shown in Reaction 4.

For example, a xylene suspension (150 mL) of arylamine Compound 53 (5.16 g, 14.3 mmol), bromobiphenyl Compound 44 (3.68 g, 15.8 mmol), tris(dibenzylideneacetone)bispalladiumchloroform addition product (Pd$_2$(dba)$_3$-CHCl$_3$) (446 mg, 0.432 mmol), sodium tert-butoxide (4.15 g, 43.2 mmol), and tri-tert-butylphosphine (1.65 M toluene solution) (0.52 mL, 0.86 mmol) was refluxed while stirring under an argon atmosphere for 8 hours. The reaction product was filtered using Florisil®, and the filtrate was concentrated. The residue was separated by column chromatography to produce the monoamine derivative of Compound 1 (6.24 g, yield 85%) according to an embodiment of the present disclosure.

The molecular weight of Compound 1 was measured using fast atom bombardment-mass spectrometry (FAB-MS). The molecular weight was 511, coinciding with the calculated value of Compound 1 from the molecular formula of C$_{38}$H$_{25}$NO, and the structure of Compound 1 was thereby identified.

(Synthesis of Compound 4)

Compound 4, a monoamine derivative according to an embodiment of the present disclosure, was synthesized according to Reaction 5:

Compound 4 was synthesized via reaction of arylamine Compound 51 with halogenated aryl Compound 52 using a Pd-based catalyst to first produce intermediate Compound 53, as shown in Reaction 5. The synthetic method of Compound 53 was substantially the same as that described for the synthesis of Compound 1, and a detailed description thereof will not be provided.

Next, intermediate arylamine Compound 53 was reacted with halogenated aryl Compound 54 using a Pd-based catalyst to synthesize the monoamine Compound 4 according to an embodiment of the present disclosure, as shown in Reaction 5.

For example, a xylene suspension (150 mL) of arylamine Compound 53 (4.57 g, 12.7 mmol), bromophenylnaphthalene Compound 54 (3.96 g, 14.0 mmol), tris(dibenzylideneacetone)bispalladium chloroform adduct (395 mg, 0.382 mmol), sodium Pert-butoxide (3.67 g, 38.2 mmol), and tri-tert-butylphosphine (1.65 M toluene solution) (0.46 mL, 0.76 mmol) was refluxed while stirring under an argon atmosphere for 8 hours. The reaction product was filtered using Florisil®, and the filtrate was concentrated. The residue was separated by column chromatography to produce Compound 4 (6.45 g, yield 90%) according to an embodiment of the present disclosure.

The molecular weight of Compound 4 as measured by FAB-MS was 561, which coincides with the calculated value of Compound 4 from the molecular formula of $C_{42}H_{27}NO$, and the structure of Compound 4 was thereby identified.

Chemical shift values of Compound 4 measured by $^1$H-NMR (300 MHz, CDCl$_3$ [ppm]) were 8.78 (d, 1H, J=8.3 Hz), 8.17 (dd, 1H, J=1.0, 8.2 Hz), 8.03 (m, 1H), 7.89 (m, 1H), 7.80-7.86 (3H), 7.78 (s, 1H), 7.77 (d, 1H, J=8.4 Hz), 7.56-7.72 (3H), 7.27-7.56 (13H), 7.20 (dd, 1H, J=2.0, 8.4 Hz).

(Synthesis of Compound 6)

Compound 6, a monoamine derivative according to an embodiment of the present disclosure, was synthesized according to Reaction 6. Substantially the same procedure as Reaction 5 was conducted, except for using bromoterphenyl Compound 64 instead of bromophenylnaphthalene Compound 54. The molecular weight of Compound 6 as measured by FAB-MS was 623, which coincides with the calculated value of Compound 6 from the molecular formula of $C_{44}H_{29}NO$, and the structure of Compound 6 was thereby identified.

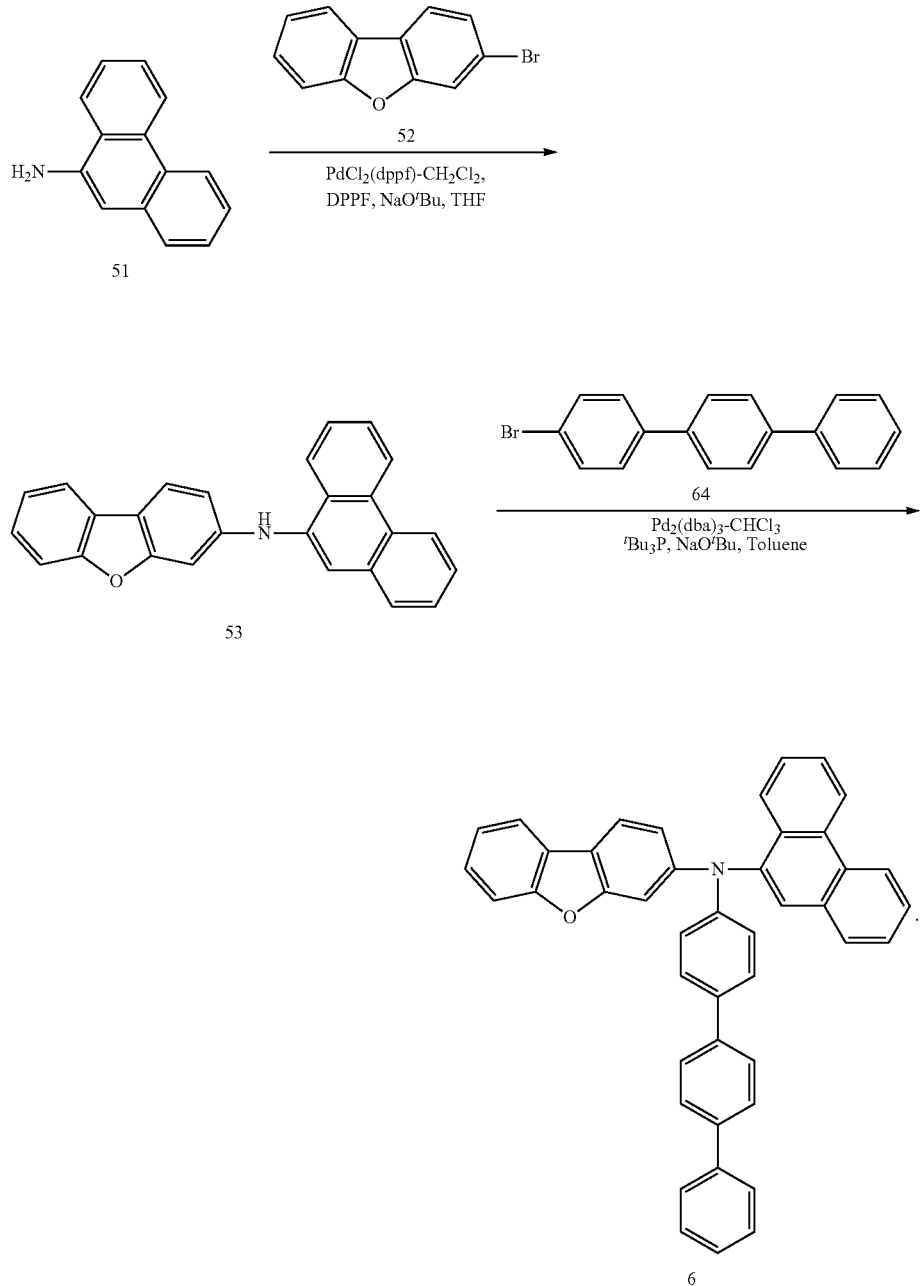

(Synthesis of Compound 7)

Compound 7, a monoamine derivative according to an embodiment of the present disclosure, was synthesized according to Reaction 7. Substantially the same procedure as Reaction 5 was conducted, except for using bromoterphenyl Compound 74 instead of using bromophenylnaphthalene Compound 54. The molecular weight of Compound 7 as measured by FAB-MS was 623, which coincides with the calculated value of Compound 7 from the molecular formula of $C_{44}H_{29}NO$, and the structure of Compound 7 was thereby identified.

[Reaction 7]

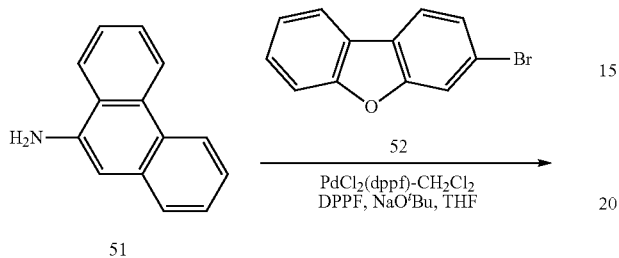

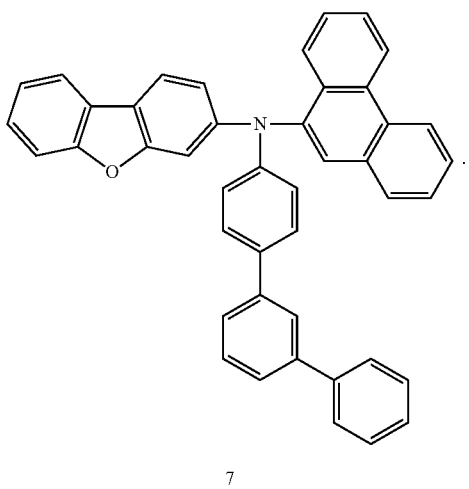

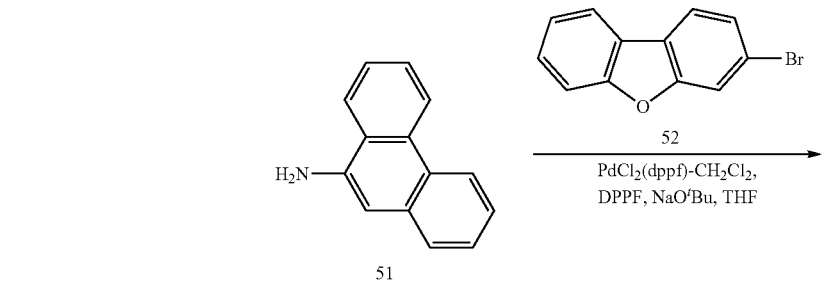

(Synthesis of Compound 34)

Compound 34, a monoamine derivative of according to an embodiment of the present disclosure, was synthesized according to Reaction 8. Substantially the same procedure as Reaction 5 was conducted, except for using Compound 84 instead of using bromophenylnaphthalene Compound 54. The molecular weight of Compound 34 as measured by FAB-MS was 751, which coincides with the calculated value of Compound 34 from the molecular formula of $C_{57}H_{37}NO$, and the structure of Compound 34 was thereby identified.

[Reaction 8]

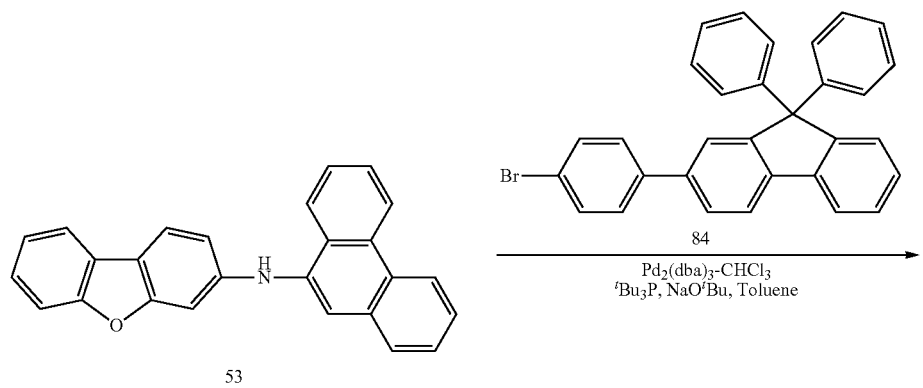

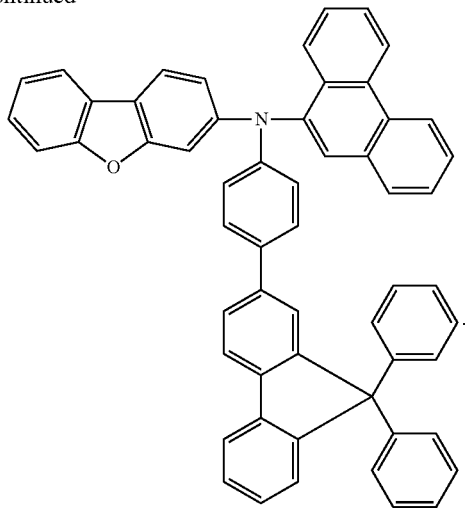
34

[Manufacture of Organic Electroluminescent Device Including Amine Derivative]

An organic electroluminescent device including the amine derivative as a hole transport material, according to an embodiment of the present disclosure, was manufactured using vacuum deposition according to the following method:

Example 1

An ITO-glass substrate was patterned and washed in advance, and then surface treated using ultraviolet rays and ozone ($O_3$). The thickness of the ITO layer (e.g., the first electrode) in the glass substrate was about 150 nm. After surface treatment, the substrate was washed and injected into an evaporator for forming an organic layer, and a hole injection layer, a hole transport layer (HTL), an emission layer, and an electron transport layer were vacuum deposited one by one at a vacuum degree of about $10^{-4}$ to about $10^{-5}$ Pa.

The material of the hole injection layer was 4,4',4"-tris(N,N-2-naphthylphenylamino) triphenylamine (2-TNATA), and the thickness thereof was about 60 nm. The hole transport layer was formed using Compound 1 to a thickness of about 30 nm. The emission layer included 9,10-di(2-naphthyl)anthracene (ADN) as a host material and 2,5,8,11-tetra-t-butylperylene (TBP) as a dopant material, and was formed to a thickness of about 25 nm. The doping amount of the dopant was about 3% (volume/volume) with respect to the host material. The electron transport layer was formed using $Alq_3$ to a thickness of about 25 nm.

The substrate was subsequently transferred to an evaporator for forming a metal layer, and an organic electroluminescent device was manufactured by vacuum depositing an electron injection layer and a second electrode at a vacuum degree of about $10^{-4}$ to about $10^{-5}$ Pa. The material of the electron injection layer was LiF, and the thickness thereof was about 1 nm. The material of the second electrode was Al, and the thickness thereof was about 100 nm.

Example 2

An organic electroluminescent device was manufactured by conducting the same procedure described in Example 1, except for forming the hole transport layer (HTL) using Compound 4.

Example 3

An organic electroluminescent device was manufactured by conducting the same procedure described in Example 1, except for forming the hole transport layer (HTL) using Compound 6.

Example 4

An organic electroluminescent device was manufactured by conducting the same procedure described in Example 1, except for forming the hole transport layer (HTL) using Compound 7.

Example 5

An organic electroluminescent device was manufactured by conducting the same procedure described in Example 1, except for forming the hole transport layer (HTL) using Compound 34.

Comparative Example 1

An organic electroluminescent device was manufactured by conducting the same procedure described in Example 1, except that the hole transport layer (HTL) was formed using Comparative Compound C1. Comparative Compound C1 differs from the monoamine derivative according to an embodiment of the present disclosure in that the nitrogen atom of a monoamine derivative is combined (e.g., coupled) with dibenzofuran via a phenylene group.

Comparative Example 2

An organic electroluminescent device was manufactured by conducting the same procedure described in Example 1, except that the hole transport layer (HTL) was formed using Comparative Compound C2. Comparative Compound C2 differs from the monoamine derivative according to an embodiment of the present disclosure in that the nitrogen atom of a monoamine derivative is combined (e.g., coupled) with carbon at position 2 of a phenanthrene group.

Comparative Example 3

An organic electroluminescent device was manufactured by conducting the same procedure described in Example 1, except that the hole transport layer (HTL) was formed using Comparative Compound C3. Comparative Compound C3 differs from the monoamine derivative according to an embodiment of the present disclosure in that the nitrogen atom of a monoamine derivative is combined (e.g., coupled) with dibenzofuran via a phenylene group.

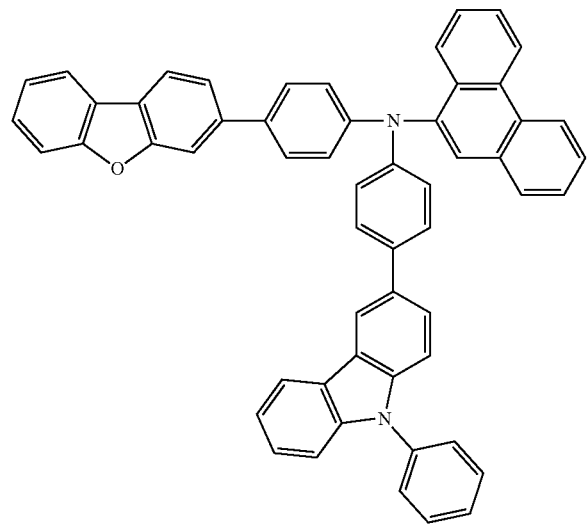

C1

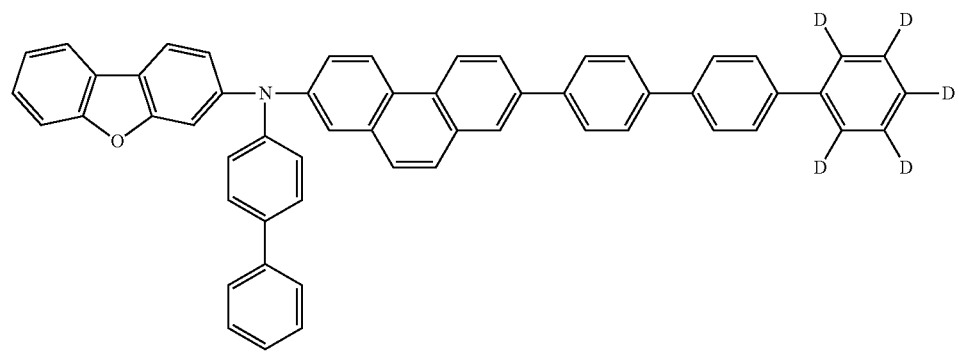

C2

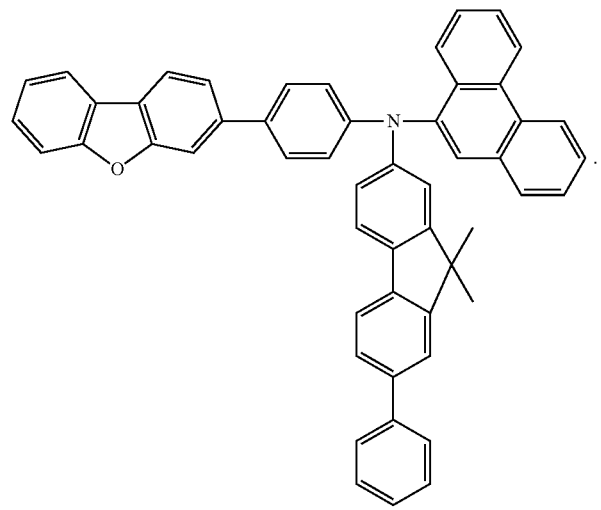

C3

Evaluation Results

Evaluation results for the organic electroluminescent devices according to Examples 1 to 5 and Comparative Examples 1 to 3 are shown in Table 1. The emission properties of the organic electroluminescent devices thus manufactured were evaluated using the C9920-11 Brightness Light Distribution Characteristics Measurement System of HAMAMATSU Photonics Co. In Table 1, the reported half life, measured at a constant current density, indicates the time (LT50) elapsed between initial light emission (at about 1,000 cd/m$^2$) and the point when the luminescence of the organic electroluminescent device became half of the initial measurement. The results of Examples 1 to 5 and Comparative Examples 1 to 3 are expressed as relative ratios, wherein the result of Comparative Example 1 was normalized to a value of 1.

TABLE 1

| Organic electroluminescent device | Hole transport layer | Half life (relative ratio) |
|---|---|---|
| Example 1 | Compound 1 | 1.7 |
| Example 2 | Compound 4 | 1.5 |
| Example 3 | Compound 6 | 1.8 |
| Example 4 | Compound 7 | 1.6 |
| Example 5 | Compound 34 | 1.3 |
| Comparative Example 1 | Comparative Compound C1 | 1 |
| Comparative Example 2 | Comparative Compound C2 | 0.8 |
| Comparative Example 3 | Comparative Compound C3 | 0.8 |

Referring to Table 1, the emission lifetimes of Examples 1 to 5 including the monoamine derivative according to an embodiment of the present disclosure in the hole transport layer (HTL) were improved compared to those of Comparative Examples 1 to 3.

The organic electroluminescent devices according to Examples 1 to 5, which use monoamine derivatives in which the nitrogen atom of the monoamine derivative is directly linked to dibenzofuran, have improved emission lifetimes compared to Comparative Example 1 (using Comparative Compound C1) and Comparative Example 3 (using Comparative Compound C3), which have structures in which the nitrogen atom of the monoamine derivative is combined (e.g., coupled) to a dibenzofuran via a linking phenylene group.

The organic electroluminescent devices according to Examples 1 to 5, which use monoamine derivatives in which the nitrogen atom of the monoamine derivative is coupled with the carbon at position 9 of a phenanthryl group, have improved emission lifetimes when compared to Comparative Example 2 (using Comparative Compound C2), which has a structure in which the nitrogen atom of a monoamine derivative is combined (e.g., coupled) with the carbon at position 2 of a phenanthryl group.

The emission lifetimes of the organic electroluminescent devices according to Examples 1 to 4, which use monoamine derivatives according to Formula 1 in which Ar does not include a fluorenyl group, are further improved when compared to the organic electroluminescent device according to Example 5, which uses a monoamine derivative including an Ar fluorenyl group. The organic electroluminescent devices according to Examples 1, 3, and 4 use monoamine derivatives according to Formula 1 in which Ar is a biphenyl group or a terphenyl group, and have improved emission lifetime compared to Example 2, which uses a monoamine derivative in which Ar is a phenyl naphthyl group.

As can be observed from the above results, when the monoamine derivative according to an embodiment of the present disclosure has a structure represented by Formula 1, the emission lifetimes of organic electroluminescent devices using the monoamine derivative may be improved. Therefore, the monoamine derivative according to an embodiment of the present disclosure may be put to practical use as a material for an organic electroluminescent device in one or more suitable uses of organic electroluminescent devices.

As described above, according to the present disclosure, the emission lifetime of an organic electroluminescent device may be improved.

As used herein, expressions such as "at least one of", "one of", "at least one selected from", and "one selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more example embodiments of the present disclosure have been described with reference to the drawing, it will be understood that the present disclosure should not be limited to these example embodiments, but various changes and modifications can be made by one of ordinary skill in the art within the spirit and scope of the present disclosure as defined by the following claims and equivalents thereof.

5
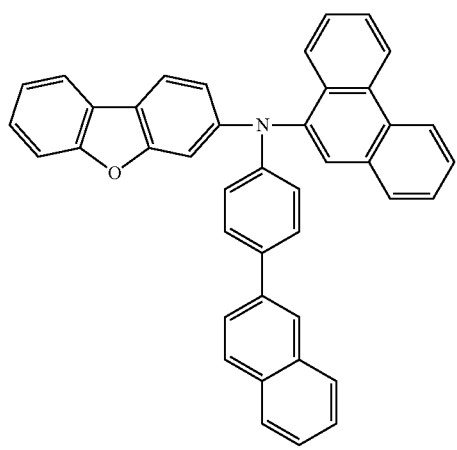
6
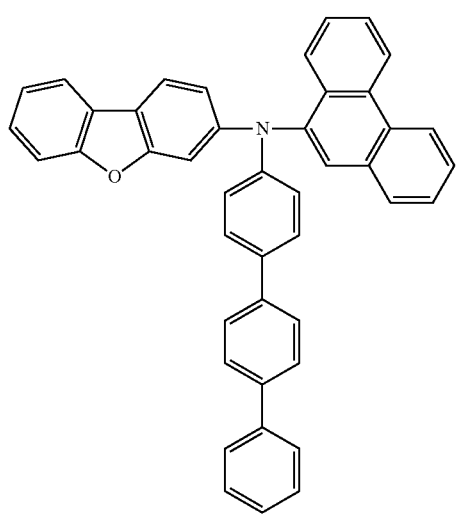
7
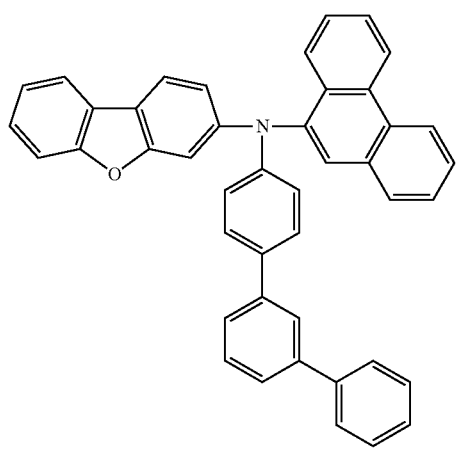
8
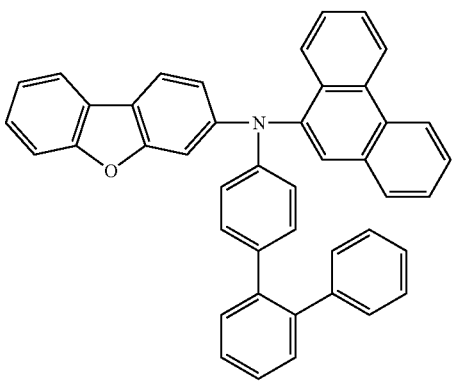
9
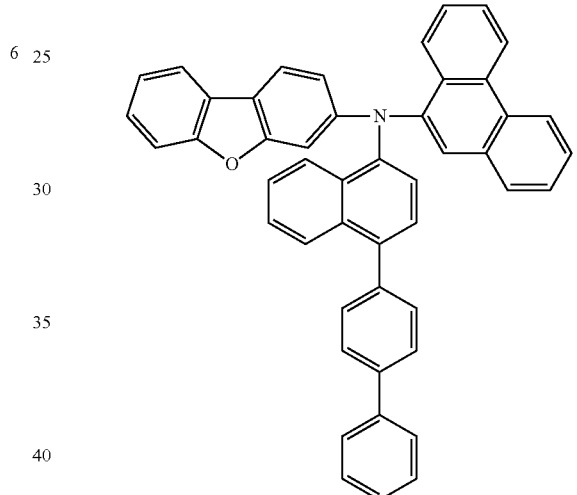
10
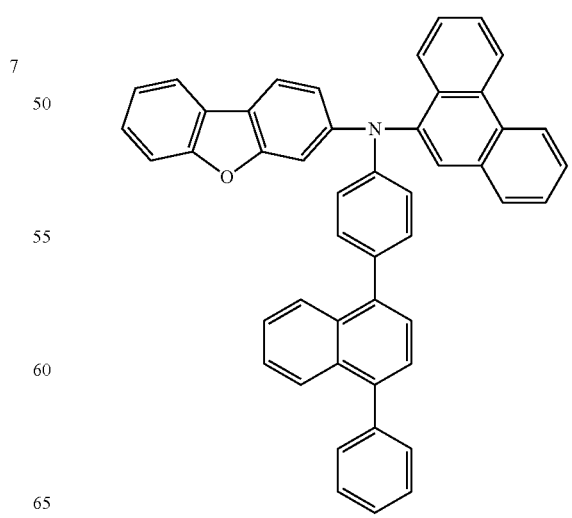

11
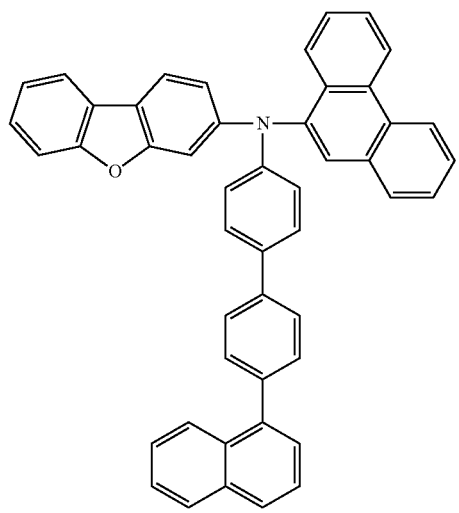
12
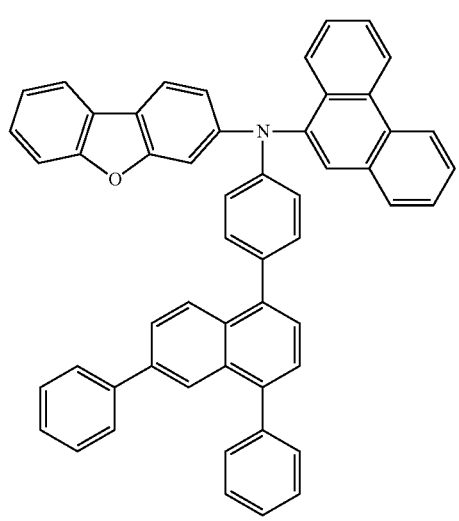
13
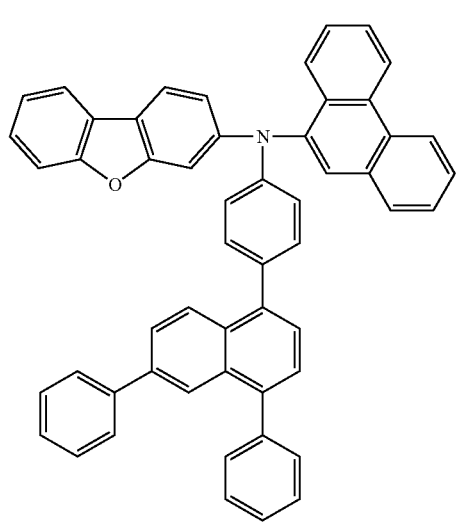
14
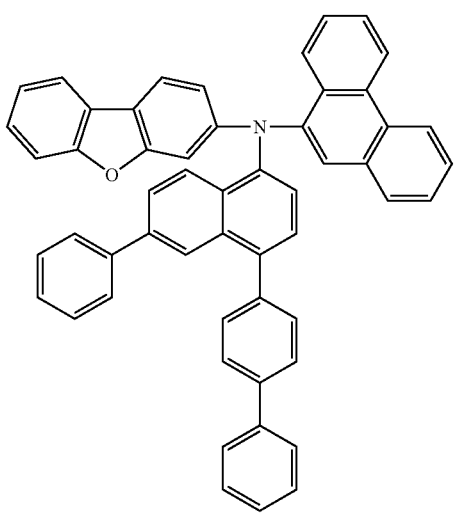
15
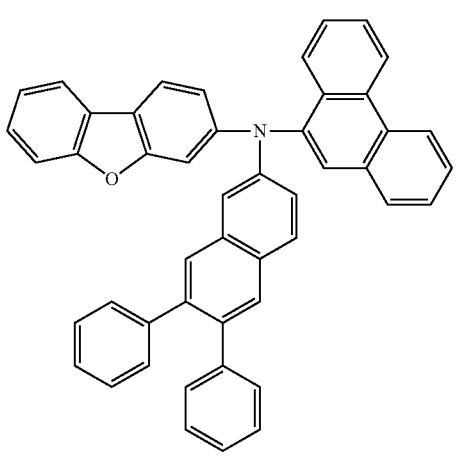
16
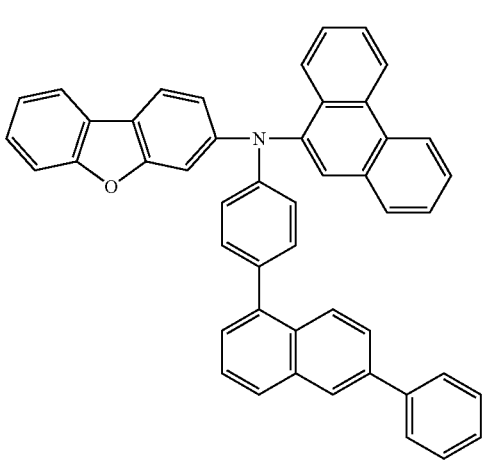

17
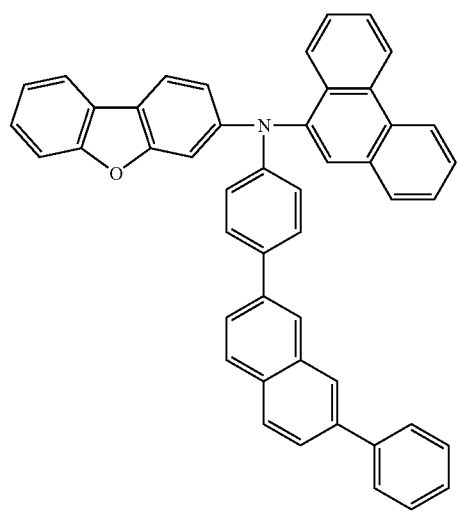
18
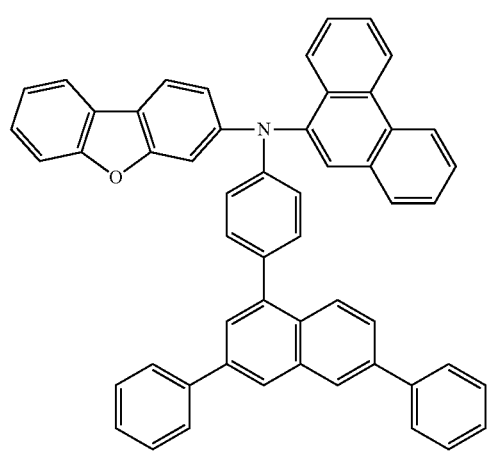
19
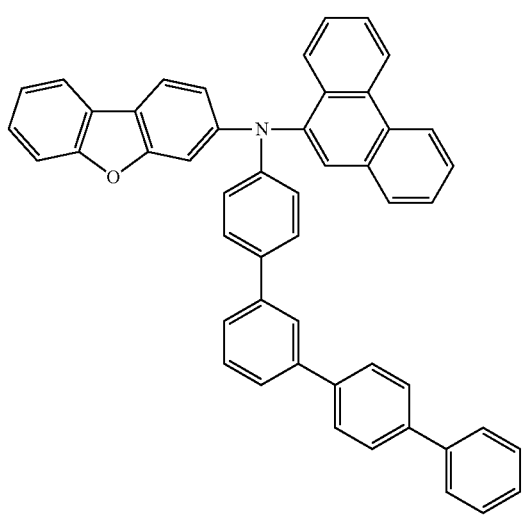
20
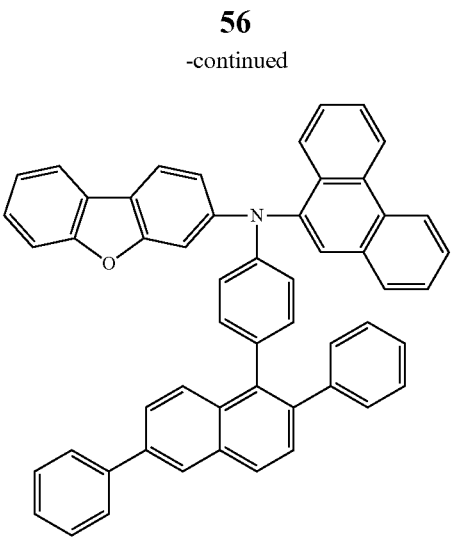
21
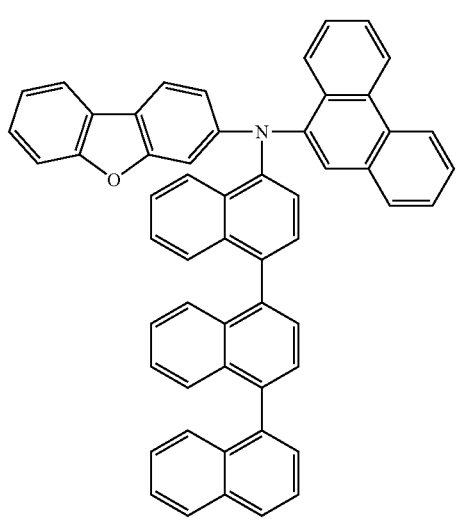
22
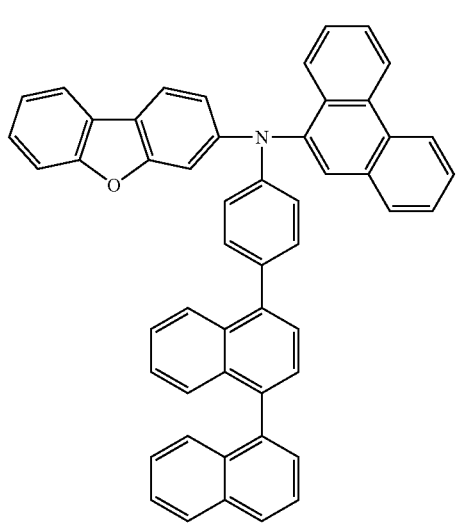

23
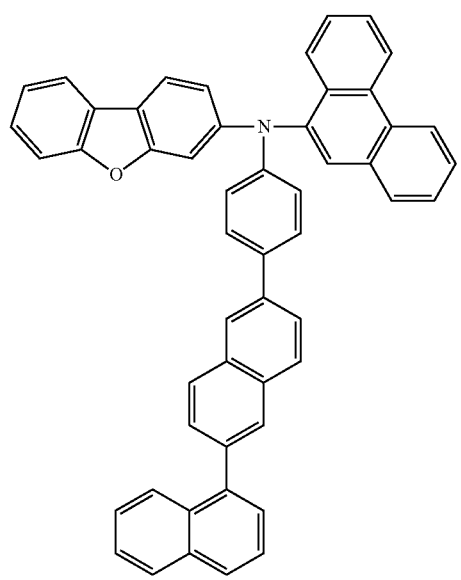
24
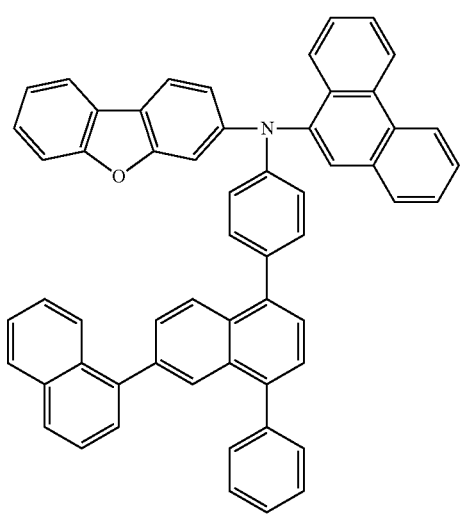
25
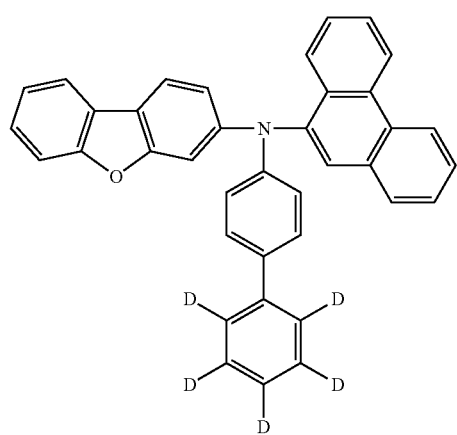
26
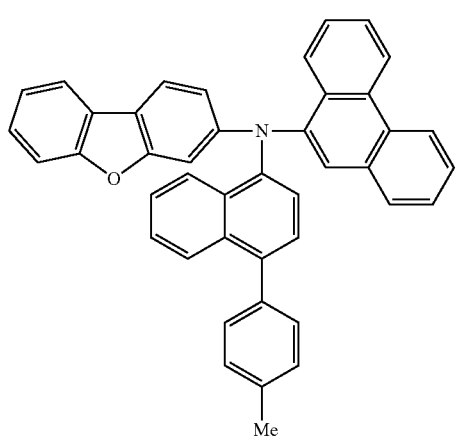
27
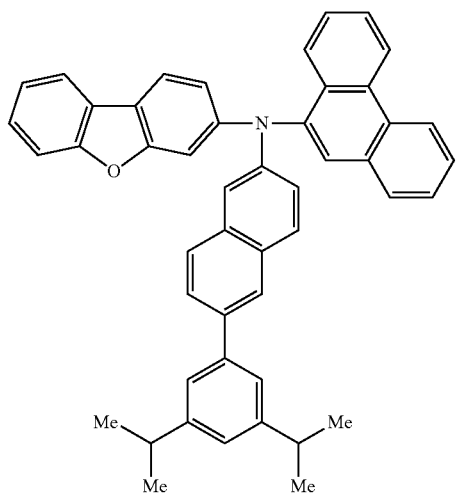
28
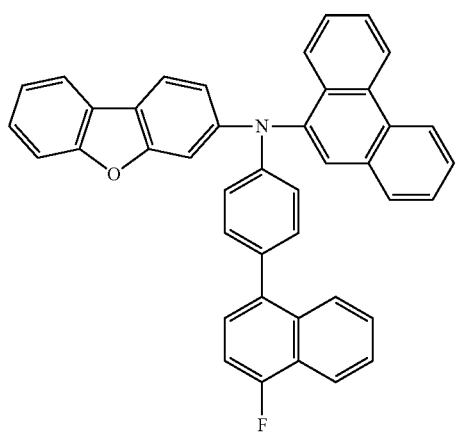

29
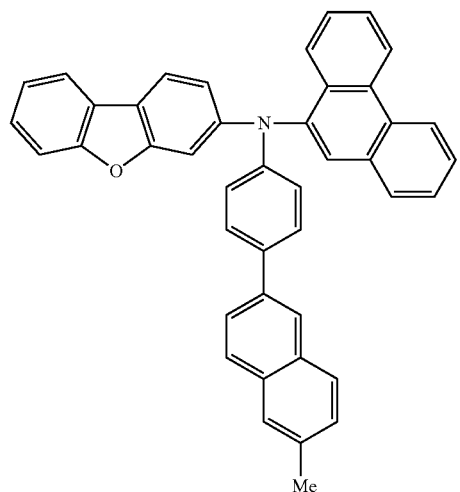
30
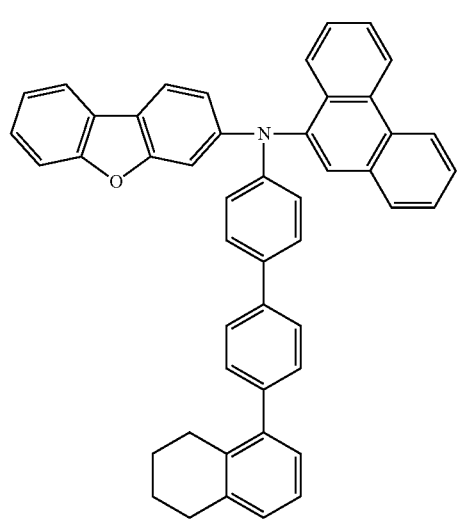
31
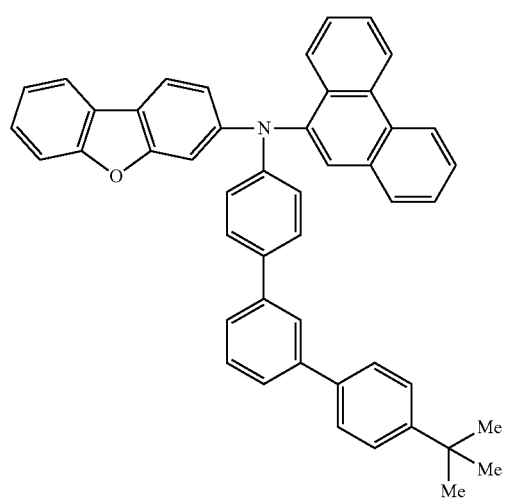
32
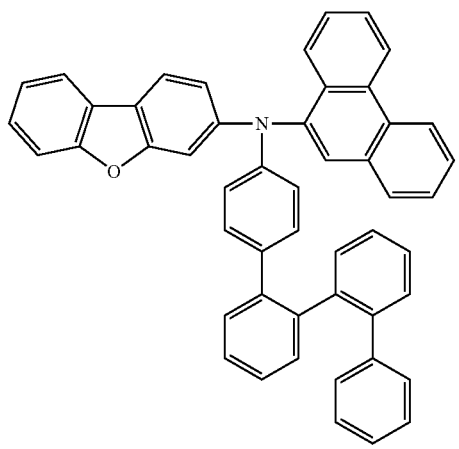
33
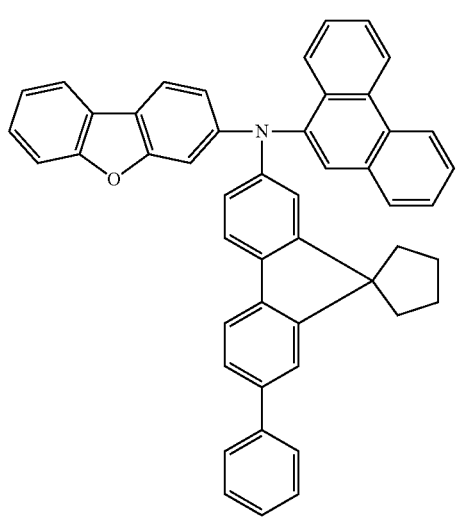
34
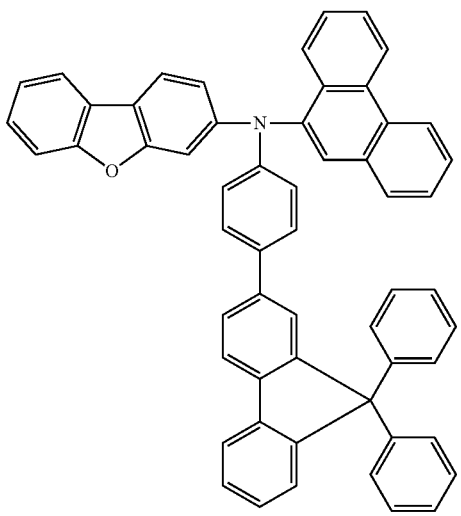

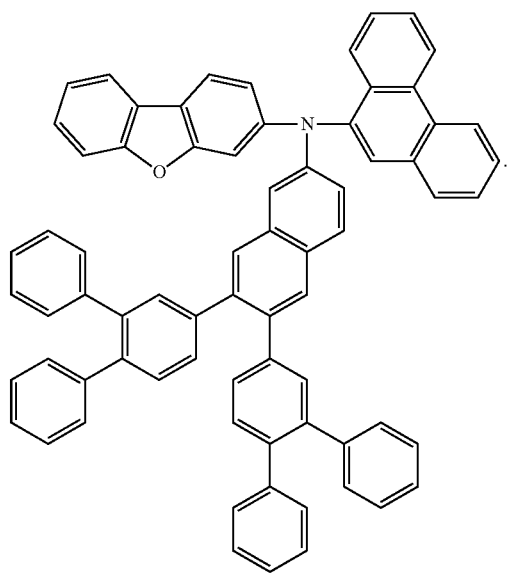

What is claimed is:

1. A material for an organic electroluminescent device, the material comprising a monoamine represented by Formula 1:

[Formula 1]

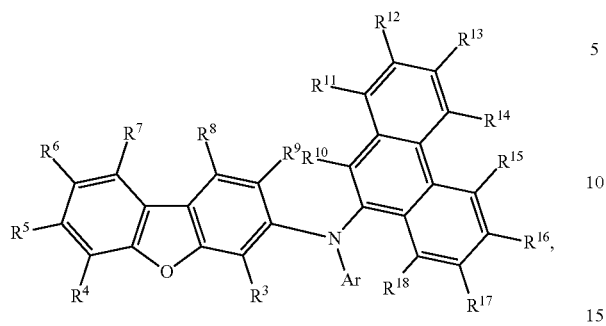

wherein, in Formula 1,

Ar is a substituted or unsubstituted aryl group having 6 to 30 carbon atoms for forming a ring, other than a substituted or unsubstituted phenanthryl group, and $R^1$ to $R^{18}$ are each independently selected from hydrogen, deuterium, a cyano group, a fluorine group, a substituted or unsubstituted alkyl group having 1 to 10 carbon atoms, and a substituted or unsubstituted aryl group having 6 to 30 carbon atoms for forming a ring.

2. The material for an organic electroluminescent device of claim 1, wherein Ar is an aryl group other than an aryl-substituted phenyl group.

3. The material for an organic electroluminescent device of claim 1, wherein Ar is a substituted or unsubstituted phenyl group, biphenyl group, terphenyl group, or quaterphenyl group.

4. The material for an organic electroluminescent device of claim 1, wherein Ar is a substituted or unsubstituted naphthyl group, naphthyl phenyl group, ternaphthyl group, binaphthyl group, or naphthyl biphenyl group.

5. The material for an organic electroluminescent device of claim 1, wherein the monoamine represented by Formula 1 is at least one selected from Compounds 1 to 35:

1

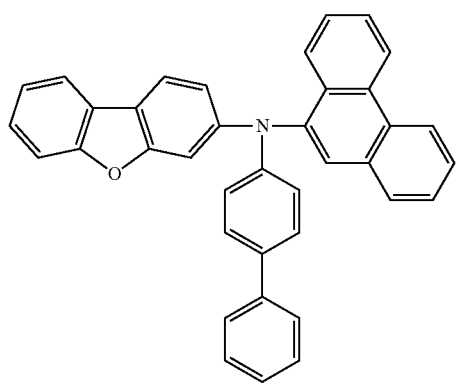

2

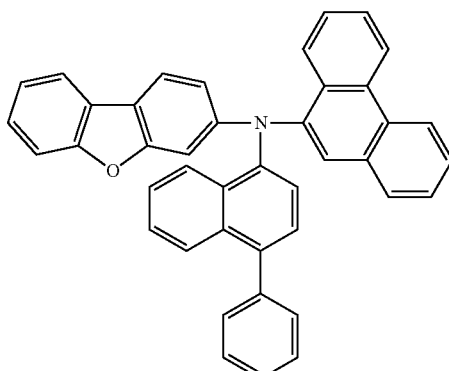

3

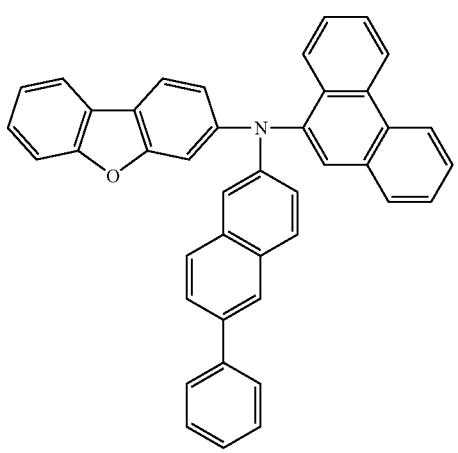

4

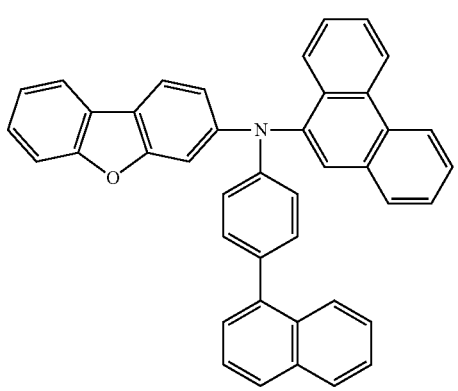

5

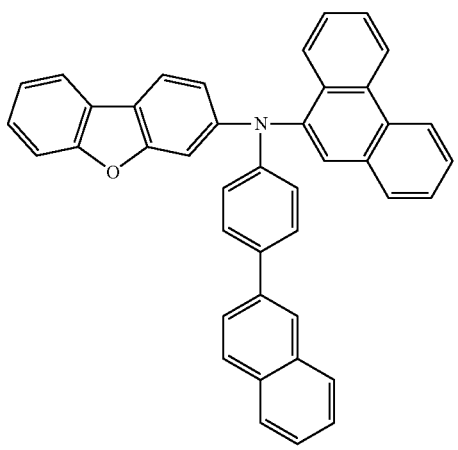

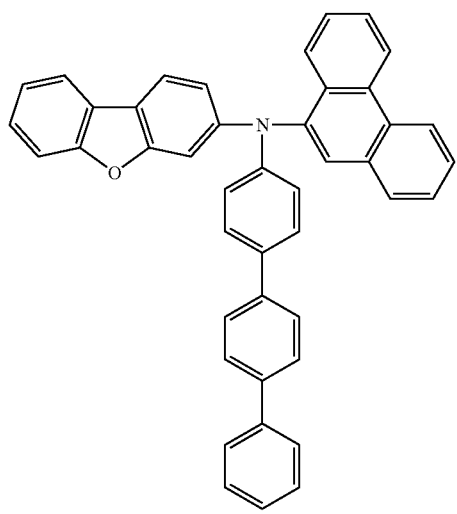
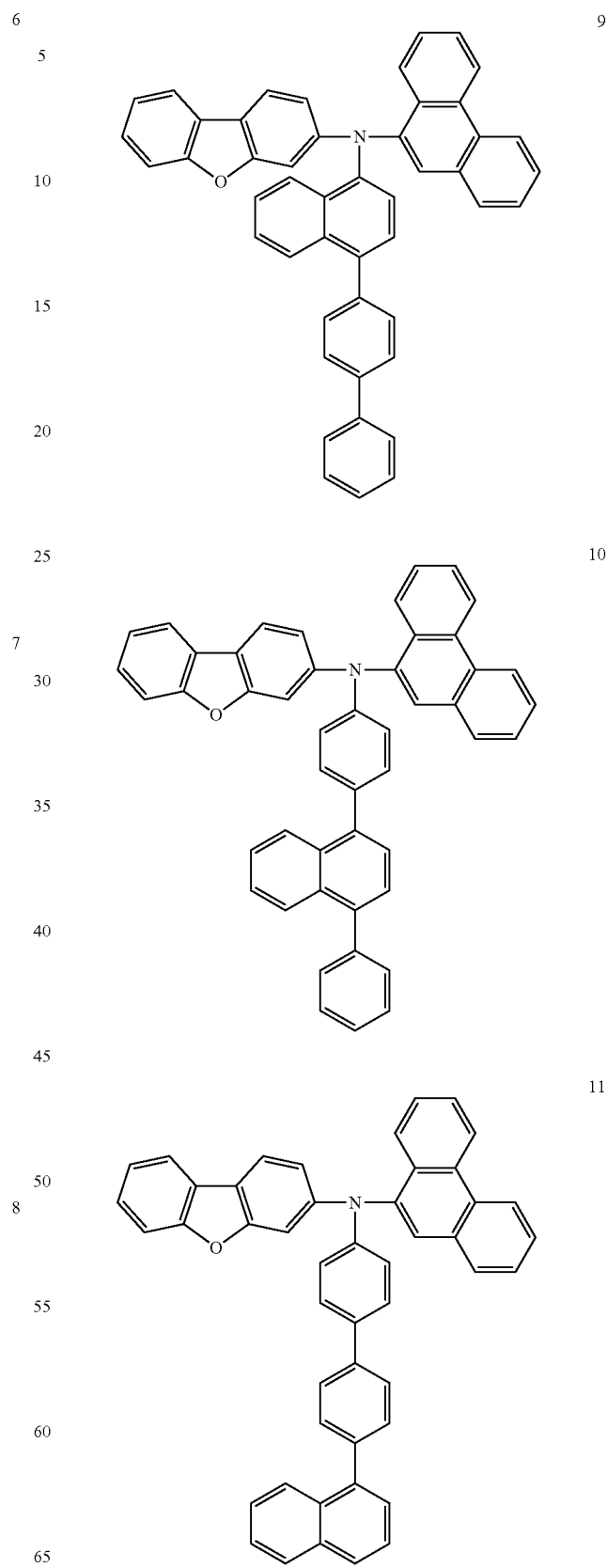

12
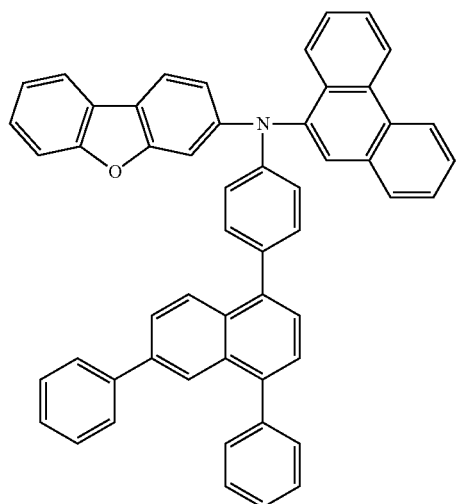
13
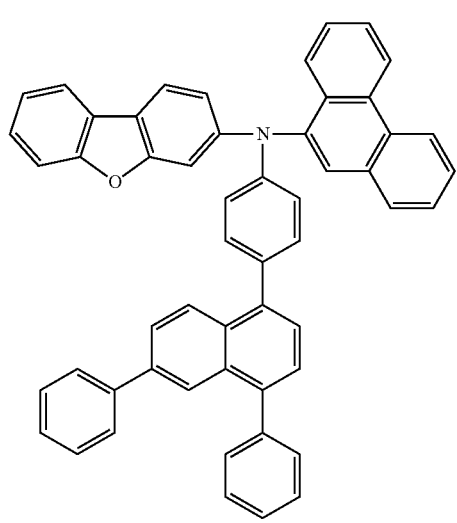
14
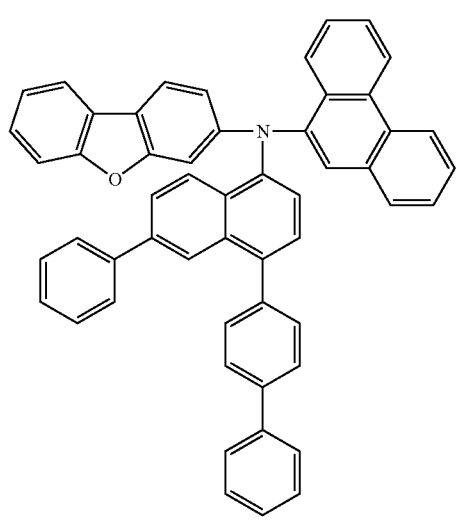
15
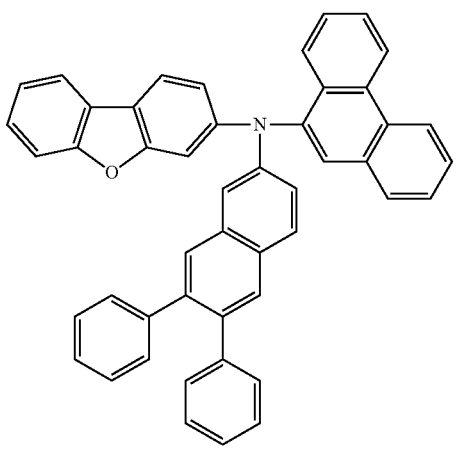
16
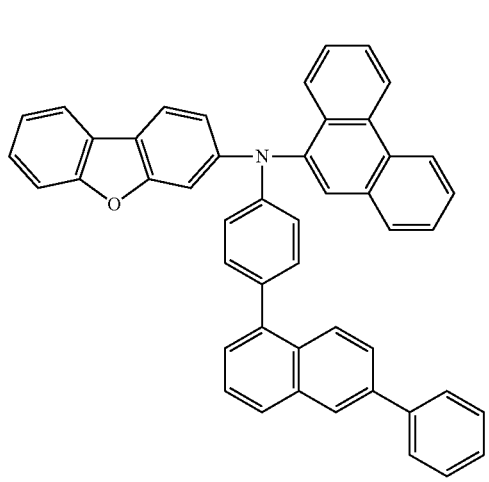
17
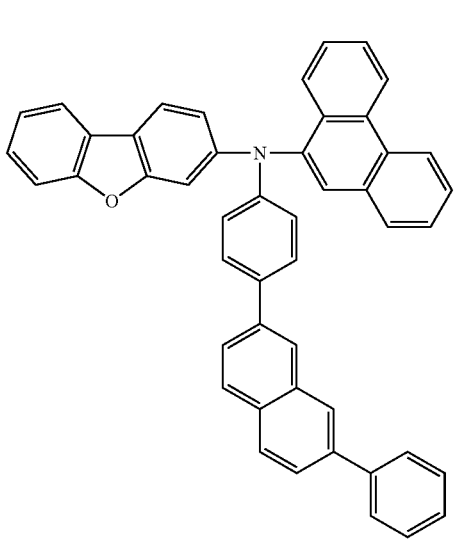

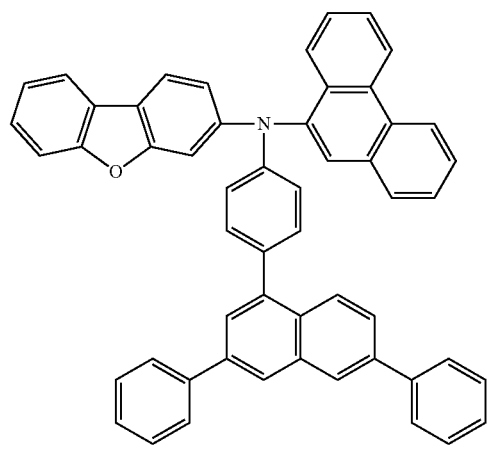
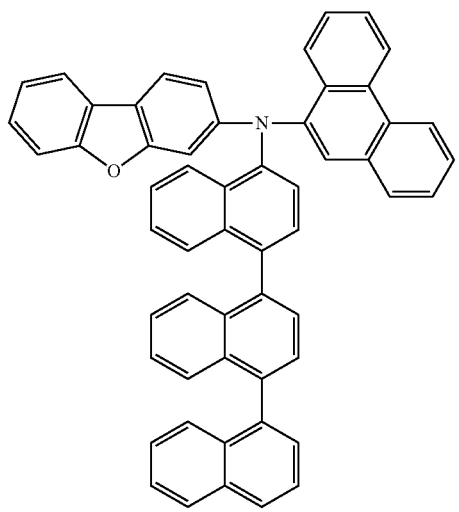
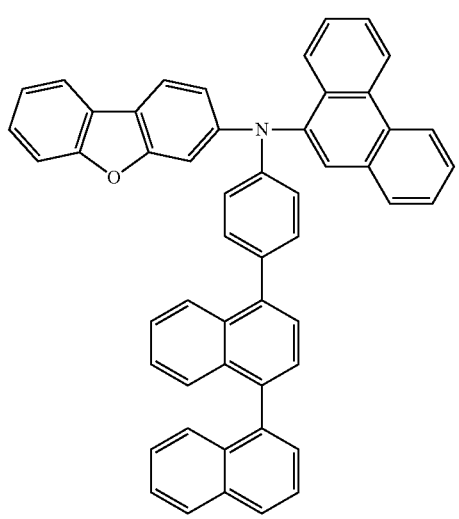
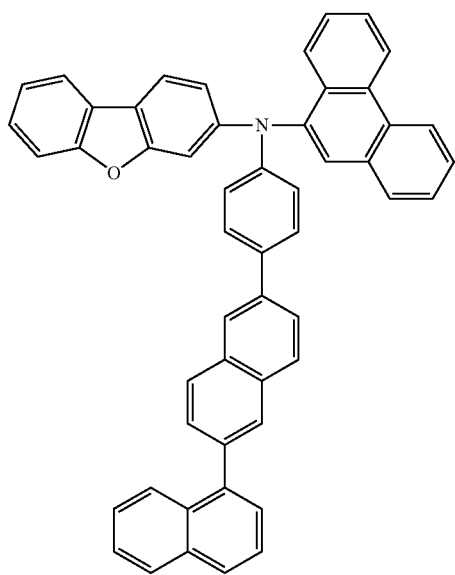

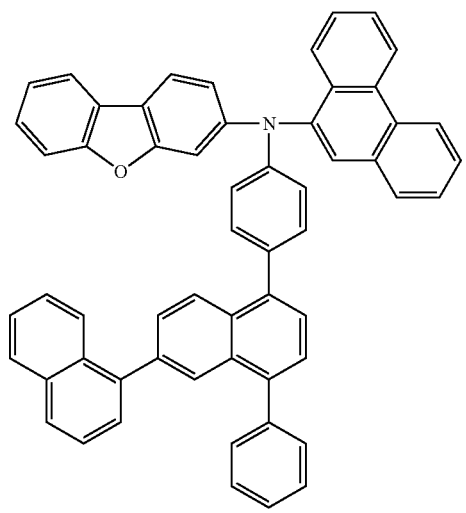
24
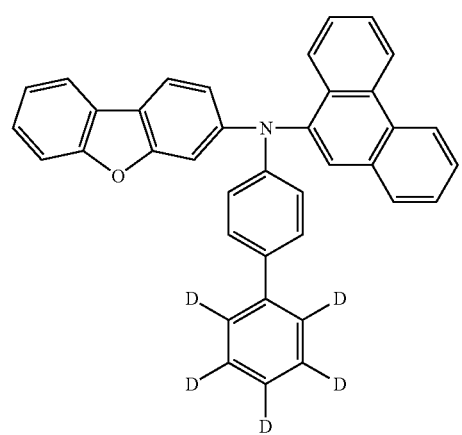
25
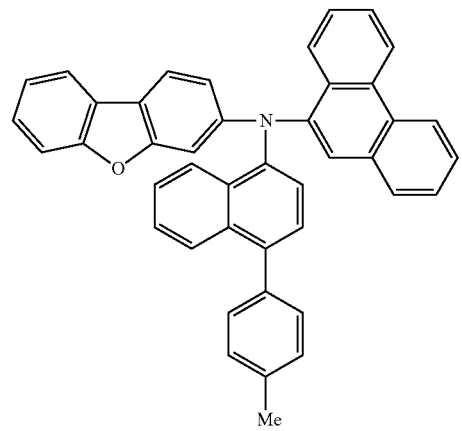
26
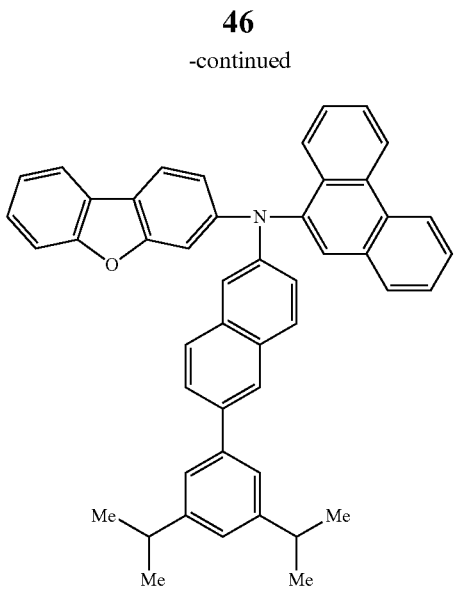
27
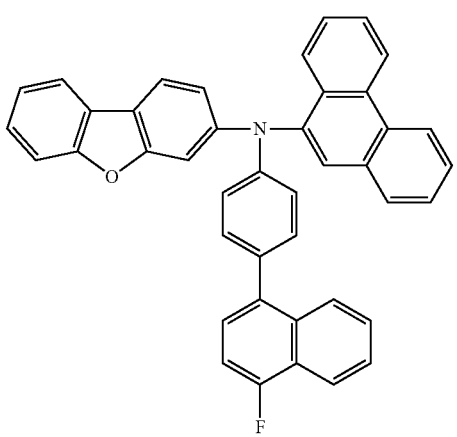
28
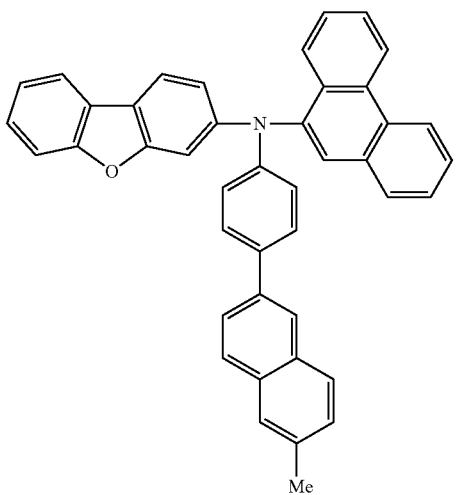
29

30
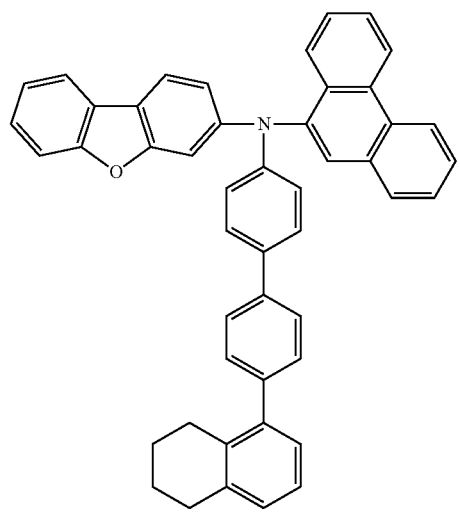
31
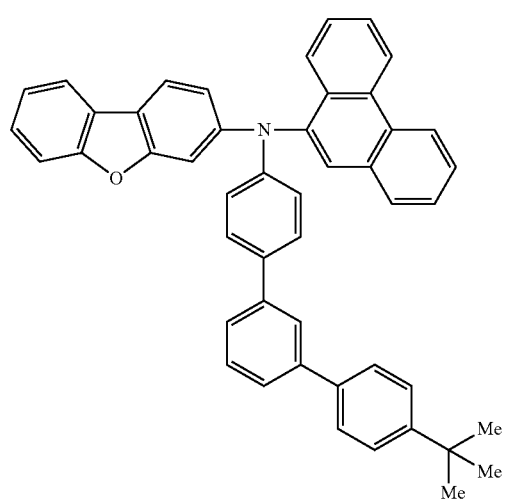
32
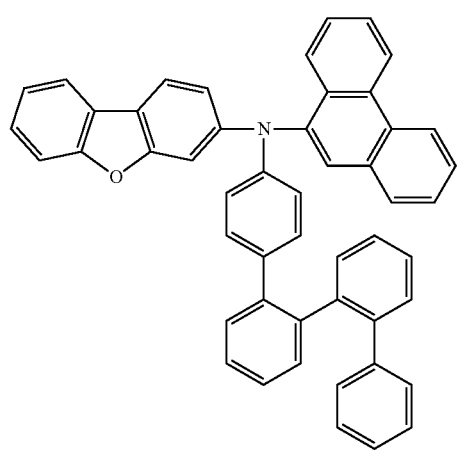
33
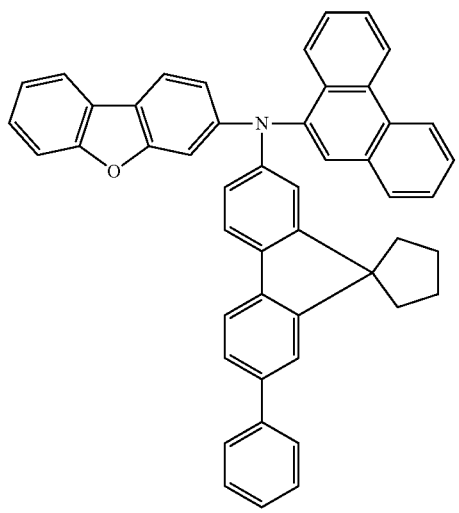
34
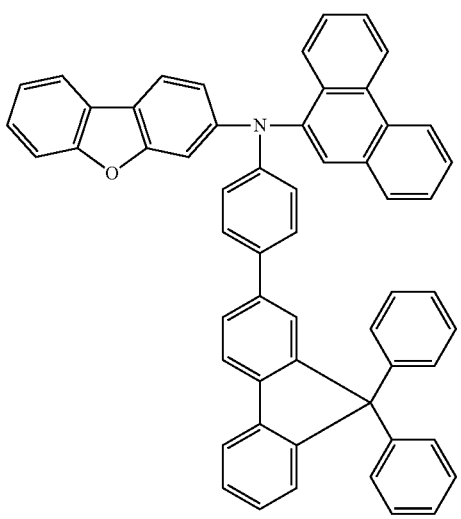
35
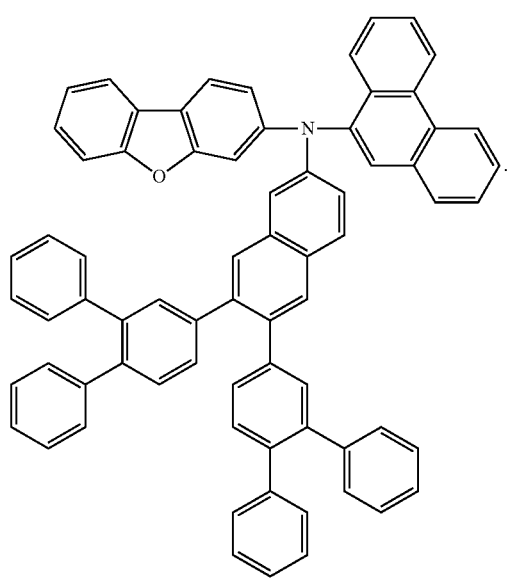

6. An organic electroluminescent device, comprising:
a first electrode;
a second electrode on the first electrode; and
one or more organic layers between the first electrode and the second electrode,
wherein at least one layer selected from the one or more organic layers comprises a material for an organic electroluminescent device, the material comprising a monoamine represented by Formula 1:

[Formula 1]

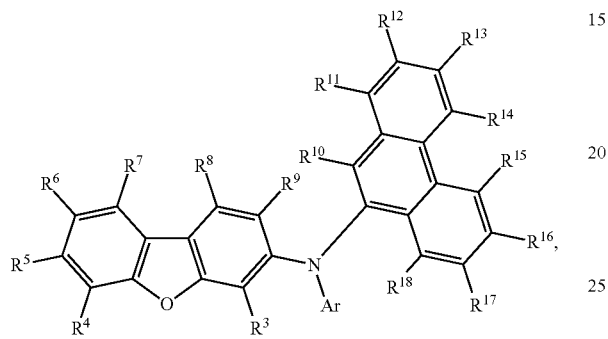

wherein, in Formula 1,
Ar is a substituted or unsubstituted aryl group having 6 to 30 carbon atoms for forming a ring, other than a substituted or unsubstituted phenanthryl group, and
$R^1$ to $R^{18}$ are each independently selected from hydrogen, deuterium, a cyano group, a fluorine group, a substituted or unsubstituted alkyl group having 1 to 10 carbon atoms, and a substituted or unsubstituted aryl group having 6 to 30 carbon atoms for forming a ring.

7. The organic electroluminescent device of claim 6,
wherein an emission layer is between the first electrode and the second electrode, and
the material for an organic electroluminescent device is included in at least one layer between the first electrode and the emission layer.

8. The organic electroluminescent device of claim 7, wherein the emission layer comprises a blue light emitting material.

9. The organic electroluminescent device of claim 6, wherein the organic layer comprising the material for an organic electroluminescent device is at least one selected from a hole injection layer and a hole transport layer.

10. The organic electroluminescent device of claim 6, wherein Ar is an aryl group other than an aryl-substituted phenyl group.

11. The organic electroluminescent device of claim 6, wherein Ar is a substituted or unsubstituted phenyl group, biphenyl group, terphenyl group, or quaterphenyl group.

12. The organic electroluminescent device of claim 6, wherein Ar is a substituted or unsubstituted naphthyl group, naphthyl phenyl group, ternaphthyl group, binaphthyl group, or naphthyl biphenyl group.

13. The organic electroluminescent device of claim 6, wherein the monoamine represented by Formula 1 is at least one selected from Compounds 1 to 35:

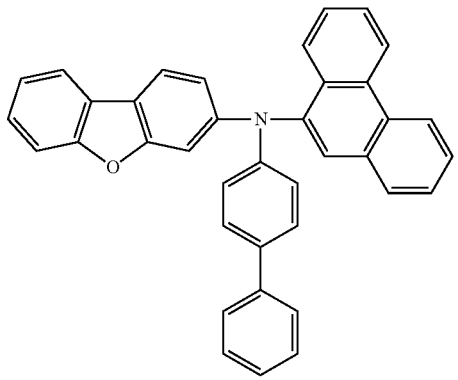

1

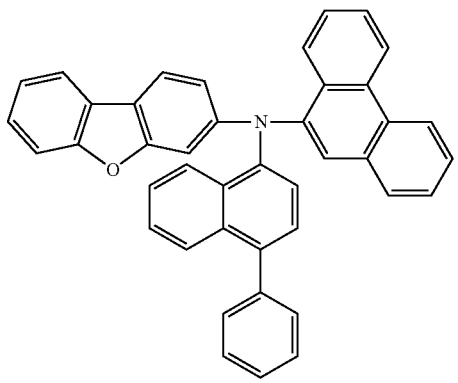

2

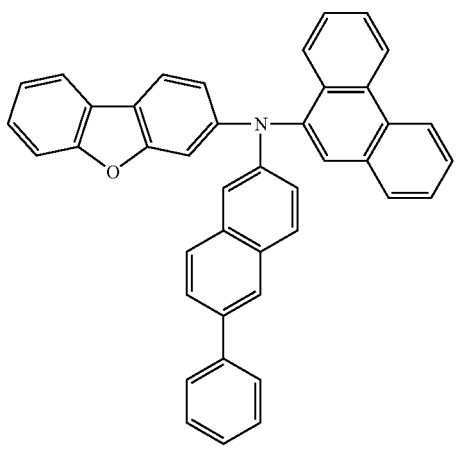

3

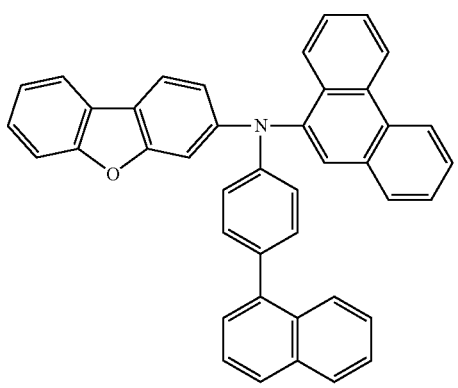

4